(12) United States Patent
Mazurov et al.

(10) Patent No.: US 8,143,272 B2
(45) Date of Patent: Mar. 27, 2012

(54) 3-SUBSTITUTED-2(ARYLALKYL)-1-AZABICYCLOALKANES AND METHODS OF USE THEREOF

(75) Inventors: Anatoly A. Mazurov, Greensboro, NC (US); Lan Miao, Advance, NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 12/636,269

(22) Filed: Dec. 11, 2009

(65) Prior Publication Data

US 2010/0152232 A1 Jun. 17, 2010

Related U.S. Application Data

(63) Continuation of application No. 11/157,119, filed on Jun. 20, 2005, which is a continuation of application No. 10/372,642, filed on Feb. 21, 2003, now Pat. No. 6,953,855.

(51) Int. Cl.
*A01N 43/90* (2006.01)
*A61K 31/519* (2006.01)

(52) U.S. Cl. ..................................... 514/305
(58) Field of Classification Search ........................ None
See application file for complete search history.

(56) References Cited

U.S. PATENT DOCUMENTS

| | | | |
|---|---|---|---|
| 4,203,990 A | 5/1980 | Yen et al. | 424/267 |
| 4,970,315 A | 11/1990 | Schmidhalter et al. | 546/10 |
| 5,212,188 A | 5/1993 | Caldwell et al. | 514/343 |
| 5,217,975 A | 6/1993 | Wadsworth et al. | 514/299 |
| 5,219,849 A | 6/1993 | Lotti et al. | 514/214 |
| 5,276,043 A | 1/1994 | Lippiello et al. | 514/343 |
| 5,346,906 A | 9/1994 | Baker et al. | 514/299 |
| 5,510,355 A | 4/1996 | Bencherif et al. | 514/305 |
| 5,583,140 A | 12/1996 | Bencherif et al. | 514/299 |
| 5,597,919 A | 1/1997 | Dull et al. | 544/242 |
| 5,604,231 A | 2/1997 | Smith et al. | 514/256 |
| 5,616,707 A | 4/1997 | Crooks et al. | 544/242 |
| 5,616,716 A | 4/1997 | Dull et al. | 546/300 |
| 5,663,356 A | 9/1997 | Ruecroft et al. | 546/300 |
| 5,811,442 A | 9/1998 | Bencherif et al. | 514/384 |
| 5,824,692 A | 10/1998 | Lippiello et al. | 514/343 |
| 5,852,041 A | 12/1998 | Cosford et al. | 514/351 |
| 5,859,004 A | 1/1999 | Olesen | 514/214 |
| 5,861,423 A | 1/1999 | Caldwell et al. | 514/351 |
| 5,952,339 A | 9/1999 | Bencherif et al. | 514/294 |
| 6,953,855 B2 | 10/2005 | Mazurov et al. | 546/135 |
| 7,425,561 B2 | 9/2008 | Mazurov et al. | 514/299 |
| 2009/0048290 A1 | 2/2009 | Dull et al. | |

FOREIGN PATENT DOCUMENTS

| | | |
|---|---|---|
| IN | 173570 | 4/1996 |
| WO | WO 91/12254 | 8/1991 |
| WO | WO 94/08992 | 4/1994 |
| WO | WO 95/03306 | 2/1995 |
| WO | WO 96/12711 | 5/1996 |
| WO | WO 97/01556 | 1/1997 |
| WO | WO 97/11072 | 3/1997 |
| WO | WO 98/25619 | 6/1998 |
| WO | WO 98/54181 | 12/1998 |
| WO | WO 99/00385 | 1/1999 |
| WO | WO 99/51602 | 10/1999 |
| WO | WO 00/34276 | 6/2000 |
| WO | WO 01/85727 | 11/2001 |

OTHER PUBLICATIONS (http://www.mentalhealth.org.uk/information/mental-health-a-z/dementia/), last accessed, Jul. 14, 2010.*
Maskell, et. al. British Journal of Pharmacology, 2003, 140(7) 1313-1319.*
Boess, et. al., The Journal of Pharmacology and Experimental Therapeutics, (2007) vol. 321, No. 2, p. 725.*
Jones, et. al., Journal of Molecular Neuroscience, 2006, 30, 83-84.*
Decker, et. al., Expert Opin. Drug Discov. (2008) 3(9) 1027-1040.*
Van Dijk, Jeanette P.M. et al., "Nicotine inhibits cytokine synthesis by mouse colonic mucosa." *European Journal of Pharmacology*, 278, R11-R12 (1995).
Hanisch, Uwe-Karsten et al., "Modulation of Hippocampal Acetylcholine Release: A Potent Central Action of Interleukin-2," *The Journal of Neuroscience*, vol. 13(8), pp. 3368-3374 (1993).
Madretsma, Stanley et al., "In-vivo effect of nicotine on cytokine production by human non-adherent mononuclear cells," *European Journal of Gastroenterology & Hepatology*, vol. 8, No. 10, pp. 1017-1020.
Madretsma, G.S., et al. "Nicotine inhibits the in vitro production of interleukin 2 and tumour necrosis factor-α by human mononuclear cells," *Immunopharmacology*, 35 pp. 47-51(1996).
Peacock, Mark E., et al., "The Effect of Nicotine on Reproduction and Attachment of Human Gingival Fibroblasts In Vitro," *J. Periodontal*, vol. 64, No. 7, pp. 658-665 (1993).
Sandborn, W.J. et al., "Nicotine tartrate liquid enemas for mildly to moderately active left-sided ulcerative colitis unresponsive to first-line therapy: a pilot study," *Ailment Pharmacol. Ther.*, 11, pp. 663-671 (1997).
Zijlstra, F. J. et al., "Effect of nicotine on rectal mucus and mucosal eicosanoids," *Gut*, 35, pp. 247-251 (1994).
Pullan, Rupert D., "Colonic mucus, smoking and ulcerative colitis," *Ann R. Coll. Surg Engl.*, 78, pp. 85-91 (1996).
Pullan, Robert D. et al., "Transdermal Nicotine for Active Ulcerative Colitis," *The New England Journal of Medicine*, vol. 330, No. 12, pp. 811-815 (1994).

(Continued)

*Primary Examiner* — Jeffrey Murray
(74) *Attorney, Agent, or Firm* — Amy H. Fix

(57) ABSTRACT

The present invention relates to 3-substituted-2-(arylalkyl)-1-azabicycloalkanes, methods of preparing the compounds and methods of treatment using the compounds. The compounds exhibit activity at nicotinic acetylcholine receptors (nAChRs), particularly the α7 nAChR subtype, and are useful towards modulating neurotransmission and the release of ligands involved in neurotransmission. Methods for preventing or treating conditions and disorders, including central nervous system (CNS) disorders, which are characterized by an alteration in normal neurotransmission, are also disclosed. Also disclosed are methods for treating inflammation, autoimmune disorders, pain and excess neovascularization, such as that associated with tumor growth.

1 Claim, No Drawings

OTHER PUBLICATIONS

Silverstein, Marc D., M.D. et al., "Cigarette Smoking and Ulcerative Colitis: A Case-Control Study," Mayo Clinic Proc., vol. 69 pp. 425-429 (1994).
Birtwistle, Jon, *Postgrad Med. J.*, "The role of cigarettes and nicotine in the onset and treatment of ulcerative colitis," vol. 72, pp. 714-718 (1996).
Ebadi, M. et al., "Neurotrophins and Their Receptors in Nerve Injury and Repair," *Neurochem Int.*, vol. 30, Nos. 4/5, pp. 347-374 (1997).
Matthys, Patrick, Ph.D., et al., "Cytokines and Cachexia," *Nutrition*, vol. 13, No. 9, pp. 763-770 (1997).
Jonakait, G. Miller, TINS, "Neural-immune interactions in sympathetic ganglia," vol. 16, No. 10, pp. 419-423 (1993).
Wallace, John L., et al., "Inflammatory Mediators in Gastrointestinal Defense and Injury," *Proc. Soc. Exp. Biol. Med.*, vol. 214, pp. 192-203 (1997).
Barnes, Peter J., Int. "Nuclear Factor-$_k$B," *J. Biochem. Cell Biol.*, vol. 29, No. 6, pp. 867-870 (1997).
Sartor, R. Balfour M.D., "Pathogenesis and Immune Mechanisms of Chronic Inflammatory Bowel Diseases," *The American Journal of Gastroenterology*, vol. 92, No. 12, pp. 5S-11S (1997).
CAS Printout for IN 173 570, Jun. 4, 1994.
CAS Printout for Schmidhalter et al., Nov. 1990.
CAS Printout for Begue et al., Dec. 1969.
Holladay, M. W. et al. *J. Med. Chem.*, vol. 40, No. 26, pp. 4169-4194 (1997).
Olesen, P.H. et al., *Bioorganic & Medicinal Chemistry Letters*, vol. 7, No. 15, pp. 1963-1968 (1997).
Yanina et al., *Khim.-Karm*, vol. 21(7), pp. 808-811 (1987).
International Search Report, PCT/US99/19906, Jan. 13, 2000.
Heeschen, Christoper, et al., "A Novel Angiogenic Pathway Mediated by Non-Neuronal Nicotinic Acetylcholine Receptors," *The Journal of Clinical Investigation*, vol. 110, No. 4, pp. 527-536 (Aug. 2002).
Tracey, Kevin J., "The Inflammatory Reflex," *Nature*, vol. 420, pp. 853-859 (Dec. 2002).
Wang, Hong, et al, "Nicotinic Acetylcholine Receptor α7 subunit is an Essential Regulator of Inflammation," *Nature*, advance online publication, Dec. 22, 2002, pp. 1-4 (Dec. 2002).
Evans, et al., Isotopic labeling with carbon-14 and tritium, *Principles of Radiopharmacology*, 1992, p. 11-13.
International Search Report (PCT/US2004/005044, dated Nov. 3, 2004).
Leiser, Steven C. et al., "A cog in cognition: How the α7 nicotinic acetylcholine receptor is geared towards improving cognitive deficits," *Pharmacology & Therapeutics*, 122 (2009) 302-311.
Young, Jared W. et al., "Nicotine Improves Sustained Attention in Mice: Evidence for Involvement of the α7 Nicotinic Acetylcholine Receptor," *Neuropsychopharmacology*, (2004) 29, 891-900.
http://schizophrenia.com/diag.php; last accessed on Nov. 9, 2009.
R. Scott Bitner, "In Vivo Pharmacological Characterization of a Novel Selective α7 Neuronal Nicotinic Acetylcholine Receptor Agonist ABT-107: Preclinical Considerations in Alzheimer's Disease", The Journal of Pharmacology and Experimental Therapeutics, 2010, vol. 334, No. 3:875.886.
Robert S. Bitner, "Broad-Spectrum Efficacy across Cognitive Domains by α7 Nicotinic Acetylcholine Receptor Agonism Correlates with Activation of ERK1/2 and CREB Phosphorylation Pathways", The Journal of Neuroscience, Sep. 26, 2007; 27(39):10578-10587.
Williams et al., *DN&P*, 7(4): 205-223, May 1994.
Arneric et al., *Alzheimer Disease and Associated Disorders*, vol. 9, Suppl. 2, pp. 50-61 (1995).
Levin and Rezvani, *Current Drug Targets: CNS and Neurological Disorders* 1(4): 1 423 (2002).
Dorwald, F.Z., *Side Reactions in Organic Synthesis; A Guide to Successful Syntheses Design*, p. IX of Preface (2006).

* cited by examiner

3-SUBSTITUTED-2(ARYLALKYL)-1-AZABICYCLOALKANES AND METHODS OF USE THEREOF

CROSS REFERENCE TO RELATED APPLICATIONS

This application is a continuation of U.S. Ser. No. 11/157,119, filed Jun. 20, 2005, pending, which is a continuation of U.S. Ser. No. 10/372,642, filed on Feb. 21, 2003, now U.S. Pat. No. 6,953,855, each of which is incorporated herein by reference in its entirety.

FIELD OF THE INVENTION

The present invention relates to pharmaceutical compositions incorporating compounds capable of affecting nicotinic acetylcholinergic receptors (nAChRs), for example, as modulators of specific nicotinic receptor subtypes (specifically, the α7 nAChR subtype). The present invention also relates to methods for treating a wide variety of conditions and disorders, particularly those associated with dysfunction of the central and autonomic nervous systems.

BACKGROUND OF THE INVENTION

Nicotine has been proposed to have a number of pharmacological effects. See, for example, Pullan et al., *N. Engl. J. Med.* 330:811 (1994). Certain of those effects may be related to effects upon neurotransmitter release. See, for example, Sjak-shie et al., *Brain Res.* 624:295 (1993), where neuroprotective effects of nicotine are proposed. Release of acetylcholine and dopamine by neurons, upon administration of nicotine, has been reported by Rowell et al., *J. Neurochem.* 43:1593 (1984); Rapier et al., *J. Neurochem.* 50:1123 (1988); Sandor et al., *Brain Res.* 567:313 (1991) and Vizi, *Br. J. Pharmacol.* 47:765 (1973). Release of norepinephrine by neurons, upon administration of nicotine, has been reported by Hall et al., *Biochem. Pharmacol.* 21:1829 (1972). Release of serotonin by neurons, upon administration of nicotine, has been reported by Hery et al., *Arch. Int. Pharmacodyn. Ther.* 296:91 (1977). Release of glutamate by neurons, upon administration of nicotine, has been reported by Toth et al., *Neurochem Res.* 17:265 (1992). Confirmatory reports and additional recent studies have included the modulation, in the central nervous system (CNS), of glutamate, nitric oxide, GABA, tachykinins, cytokines, and peptides (reviewed in Brioni et al., *Adv. Pharmacol.* 37:153 (1997)). In addition, nicotine reportedly potentiates the pharmacological behavior of certain pharmaceutical compositions used for the treatment of certain disorders. See, for example, Sanberg et al., *Pharmacol. Biochem. & Behavior* 46:303 (1993); Harsing et al., *J. Neurochem.* 59:48 (1993) and Hughes, *Proceedings from Intl. Symp. Nic.* S40 (1994). Furthermore, various other beneficial pharmacological effects of nicotine have been proposed. See, for example, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., *JPET* 221:91(1982) and Hamon, *Trends in Pharmacol. Res.* 15:36 (1994).

Various compounds that target nAChRs have been reported as being useful for treating a wide variety of conditions and disorders. See, for example, Williams et al., *DN&P* 7(4):205 (1994); Arneric et al., *CNS Drug Rev.* 1(1):1 (1995); Arneric et al., *Exp. Opin. Invest. Drugs* 5(1):79 (1996); Bencherif et al., *JPET* 279:1413 (1996); Lippiello et al., *JPET* 279:1422 (1996); Damaj et al., *J. Pharmacol. Exp. Ther.* 291:390 (1999); Chiari et al., *Anesthesiology* 91:1447 (1999); Lavand'homme and Eisenbach, *Anesthesiology* 91:1455 (1999); Holladay et al., *J. Med. Chem.* 40(28): 4169 (1997); Bannon et al., *Science* 279: 77 (1998); PCT WO 94/08992, PCT WO 96/31475, PCT WO 96/40682, and U.S. Pat. No. 5,583,140 to Bencherif et al., U.S. Pat. No. 5,597,919 to Dull et al., U.S. Pat. No. 5,604,231 to Smith et al., and U.S. Pat. No. 5,852,041 to Cosford et al. Nicotinic compounds are reported as being particularly useful for treating a wide variety of CNS disorders. Indeed, a wide variety of compounds have been reported to have therapeutic properties. See, for example, Bencherif and Schmitt, *Current Drug Targets: CNS and Neurological Disorders* 1(4): 349 (2002), Levin and Rezvani, *Current Drug Targets: CNS and Neurological Disorders* 1(4): 423 (2002), O'Neill et al., *Current Drug Targets: CNS and Neurological Disorders* 1(4): 399 (2002), U.S. Pat. No. 5,187,166 to Kikuchi et al., U.S. Pat. No. 5,672,601 to Cignarella, PCT WO 99/21834, and PCT WO 97/40049, UK Patent Application GB 2295387, and European Patent Application 297,858.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine and/or serotonin. Relatively common CNS disorders include presenile dementia (early-onset Alzheimer's disease), senile dementia (dementia of the Alzheimer's type), micro-infarct dementia, AIDS-related dementia, Creutzfeld-Jakob disease, Pick's disease, Parkinsonism including Parkinson's disease, Lewy body dementia, progressive supranuclear palsy, Huntington's chorea, tardive dyskinesia, hyperkinesia, mania, attention deficit disorder, anxiety, dyslexia, schizophrenia, depression, obsessive-compulsive disorders and Tourette's syndrome.

The nAChRs characteristic of the CNS have been shown to occur in several subtypes, the most common of which are the α4β2 and α7 subtypes. See, for example, Schmitt, *Current Med. Chem.* 7: 749 (2000). Ligands that interact with the α7 nAChR subtype have been proposed to be useful in the treatment of schizophrenia. There are a decreased number of hippocampal nAChRs in postmortem brain tissue of schizophrenic patients. Also, there is improved psychological effect in smoking versus non-smoking schizophrenic patients. Nicotine improves sensory gating deficits in animals and schizophrenics. Blockade of the α7 nAChR subtype induces a gating deficit similar to that seen in schizophrenia. See, for example, Leonard et al., *Schizophrenia Bulletin* 22(3): 431 (1996). Biochemical, molecular, and genetic studies of sensory processing, in patients with the P50 auditory-evoked potential gating deficit, suggest that the α7 nAChR subtype may function in an inhibitory neuronal pathway. See, for example, Freedman et al., *Biological Psychiatry* 38(1):22 (1995).

More recently, α7 nAChRs have been proposed to be mediators of angiogenesis, as described by Heeschen et al., *J. Clin. Invest.* 100: 527 (2002). In these studies, inhibition of the α7 subtype was shown to decrease inflammatory angiogenesis. Also, α7 nAChRs have been proposed as targets for controlling neurogenesis and tumor growth (Utsugisawa et al., *Molecular Brain Research* 106(1-2): 88 (2002) and U.S. Patent Application 2002/0016371). Finally, the role of the α7 subtype in cognition (Levin and Rezvani, *Current Drug Targets: CNS and Neurological Disorders* 1(4): 423 (2002)), neuroprotection (O'Neill et al., *Current Drug Targets: CNS and Neurological Disorders* 1(4): 399 (2002) and Jeyarasasingam et al., *Neuroscience* 109(2): 275 (2002)), and neuropathic pain (Xiao et al., *Proc. Nat. Acad. Sci. (US)* 99(12): 8360 (2002)) has recently been recognized.

Various compounds have been reported to interact with α7 nAChRs and have been proposed as therapies on that basis. See, for instance, PCT WO 99/62505, PCT WO 99/03859, PCT WO 97/30998, PCT WO 01/36417, PCT WO 02/15662, PCT WO 02/16355, PCT WO 02/16356, PCT WO 02/16357, PCT WO 02/16358, PCT WO 02/17358, Stevens et al., *Psychopharm.* 136: 320 (1998), Dolle et al., *J. Labelled Comp. Radiopharm.* 44: 785 (2001) and Macor et al., *Bioorg. Med. Chem. Lett.* 11: 319 (2001) and references therein. Among these compounds, a common structural theme is that of the substituted tertiary bicylic amine (e.g., quinuclidine). Similar substituted quinuclidine compounds have also been reported to bind at muscarinic receptors. See, for instance, U.S. Pat. No. 5,712,270 to Sabb and PCTs WO 02/00652 and WO 02/051841.

It would be desirable to provide a useful method for the prevention and treatment of a condition or disorder by administering a nicotinic compound to a patient susceptible to or suffering from such a condition or disorder. It would be highly beneficial to provide individuals suffering from certain disorders (e.g., CNS diseases) with interruption of the symptoms of those disorders by the administration of a pharmaceutical composition containing an active ingredient having nicotinic pharmacology which has a beneficial effect (e.g., upon the functioning of the CNS), but does not provide any significant associated side effects. It would be highly desirable to provide a pharmaceutical composition incorporating a compound that interacts with nAChRs, such as those that have the potential to affect the functioning of the CNS. It would be highly desirable that such a compound, when employed in an amount sufficient to affect the functioning of the CNS, would not significantly affect those nAChR subtypes that have the potential to induce undesirable side effects (e.g., appreciable activity at cardiovascular and skeletal muscle receptor sites). In addition, it would be highly desirable to provide a pharmaceutical composition incorporating a compound which interacts with nicotinic receptors but not muscarinic receptors, as the latter are associated with side effects, such as hypersalivation, sweating, tremors, cardiovascular and gastrointestinal disturbances, related to the function of the parasympathetic nervous system (see Caulfield, *Pharmacol. Ther.* 58: 319 (1993) and Broadley and Kelly, *Molecules* 6: 142 (2001)). Furthermore, it would be highly desirable to provide pharmaceutical compositions, which are selective for the α7 nAChR subtype, for the treatment of certain conditions or disorders (e.g., schizophrenia, cognitive disorders, and neuropathic pain) and for the prevention of tissue damage and the hastening of healing (i.e., for neuroprotection and the control of angiogenesis). The present invention provides such compounds, compositions and methods.

SUMMARY OF THE INVENTION

The present invention relates to 3-substituted-2-(arylalkyl)-1-azabicycloalkanes, pharmaceutical compositions including the compounds, methods of preparing the compounds, and methods of treatment using the compounds. More specifically, the methods of treatment involve modulating the activity of the ζ7 nAChR subtype by administering one or more of the compounds to treat or prevent disorders mediated by the α7 nAChR subtype.

The azabicycloalkanes generally are azabicycloheptanes, azabicyclooctanes, or azabicyclononanes. The aryl group in the arylalkyl moiety is a 5- or 6-membered ring heteroaromatic, preferably 3-pyridinyl and 5-pyrimidinyl moieties, and the alkyl group is typically a $C_{1-4}$ alkyl. The substituent at the 3-position of the 1-azabicycloalkane is a carbonyl-containing functional group, such as an amide, carbamate, urea, thioamide, thiocarbamate, thiourea or similar functionality.

The compounds are beneficial in therapeutic applications requiring a selective interaction at certain nAChR subtypes. That is, the compounds modulate the activity of certain nAChR subtypes, particularly the α7 nAChR subtype, and do not have appreciable activity toward muscarinic receptors. The compounds can be administered in amounts sufficient to affect the functioning of the central nervous system (CNS) without significantly affecting those receptor subtypes that have the potential to induce undesirable side effects (e.g., without appreciable activity at ganglionic and skeletal muscle nAChR sites and at muscarinic receptors). The compounds are therefore useful towards modulating release of ligands involved in neurotransmission, without appreciable side effects.

The compounds can be used as therapeutic agents to treat and/or prevent disorders characterized by an alteration in normal neurotransmitter release. Examples of such disorders include certain CNS conditions and disorders. The compounds can provide neuroprotection, treat patients susceptible to convulsions, treat depression, autism, and certain neuroendocrine disorders, and help manage stroke patients. The compounds also are useful in treating hypertension, type II diabetes and neoplasia and effecting weight loss. As the compounds are selective for the α7 nAChR subtype, they can be used to treat certain conditions or disorders (e.g., schizophrenia, cognitive disorders, and neuropathic pain), prevent tissue damage, and hasten healing (i.e., provide neuroprotection and control of angiogenesis).

The pharmaceutical compositions provide therapeutic benefit to individuals suffering from such conditions or disorders and exhibiting clinical manifestations of such conditions or disorders. The compounds, administered with the pharmaceutical compositions, can be employed in effective amounts to (i) exhibit nicotinic pharmacology and affect relevant nAChR sites (e.g., act as a pharmacological agonists at nicotinic receptors), and (ii) modulate neurotransmitter secretion, and hence prevent and suppress the symptoms associated with those diseases. In addition, the compounds have the potential to (i) increase the number of nAChRs of the brain of the patient, (ii) exhibit neuroprotective effects and (iii) when employed in effective amounts, not cause appreciable adverse side effects (e.g., significant increases in blood pressure and heart rate, significant negative effects upon the gastro-intestinal tract, and significant effects upon skeletal muscle). The pharmaceutical compositions are believed to be safe and effective with regards to prevention and treatment of various conditions or disorders.

The foregoing and other aspects of the present invention are explained in detail in the detailed description and examples set forth below.

DETAILED DESCRIPTION OF THE INVENTION

The compounds described herein have structures that are represented by Formulas 1 and 2.

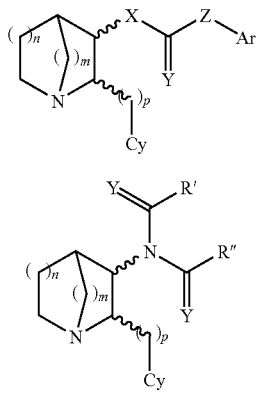

Formula 1

Formula 2

In Formulas 1 and 2, m and n individually can have a value of 1 or 2, and p can have a value of 1, 2, 3 or 4. In the Formulas, X is either oxygen or nitrogen (i.e., NR'), Y is either oxygen or sulfur, and Z is either nitrogen (i.e., NR'), a covalent bond or a linker species, A. A is selected from the group —CR'R"—, —CR'R"—, —CR'R"—, —CR'=CR'—, and —C$_2$—, wherein R' and R" are as hereinafter defined. When Z is a covalent bond or A, X must be nitrogen. Ar is an aryl group, either carbocyclic or heterocyclic, either monocyclic or fused polycyclic, unsubstituted or substituted; and Cy is a 5- or 6-membered heteroaromatic ring, unsubstituted or substituted. The wavy lines indicate that both relative and absolute stereochemistry at those sites are variable (e.g., cis or trans, R or S). The invention further includes pharmaceutically acceptable salts thereof. The compounds have one or more asymmetric carbons and can therefore exist in the form of racemic mixtures, enantiomers and diastereomers. In addition, some of the compounds exist as E and Z isomers about a carbon-carbon double bond. All these individual isomeric compounds and their mixtures are also intended to be within the scope of the present invention.

Thus, the invention includes compounds in which Ar is linked to the azabicycle by a carbonyl group-containing functionality, such as an amide, carbamate, urea, thioamide, thiocarbamate or thiourea functionality. In addition, in the case of the amide and thioamide functionalities, Ar may be bonded directly to the carbonyl (or thiocarbonyl) group or may be linked to the carbonyl (or thiocarbonyl) group through linker A. Furthermore, the invention includes compounds that contain a 1-azabicycle, containing either a 5-, 6-, or 7-membered ring and having a total of 7, 8 or 9 ring atoms (e.g., 1-azabicyclo[2.2.1]heptane, 1-azabicyclo[3.2.1]octane, 1-azabicyclo[2.2.2]octane, and 1-azabicyclo[3.2.2]nonane).

As used herein, "alkoxy" includes alkyl groups from 1 to 8 carbon atoms in a straight or branched chain, also C$_{3-8}$ cycloalkyl, bonded to an oxygen atom.

As used herein, "alkyl" includes straight chain and branched C$_{1-8}$ alkyl, preferably C$_{1-6}$ alkyl. "Substituted alkyl" defines alkyl substituents with 1-3 substituents as defined below in connection with Ar and Cy.

As used herein, "arylalkyl" refers to moieties, such as benzyl, wherein an aromatic is linked to an alkyl group which is linked to the indicated position in the compound of Formulas 1 or 2. "Substituted arylalkyl" defines arylalkyl substituents with 1-3 substituents as defined below in connection with Ar and Cy.

As used herein, "aromatic" refers to 3- to 10-membered, preferably 5- and 6-membered, aromatic and heteroaromatic rings and polycyclic aromatics including 5- and/or 6-membered aromatic and/or heteroaromatic rings.

As used herein, "aryl" includes both carbocyclic and heterocyclic aromatic rings, both monocyclic and fused polycyclic, where the aromatic rings can be 5- or 6-membered rings. Representative monocyclic aryl groups include, but are not limited to, phenyl, furanyl, pyrrolyl, thienyl, pyridinyl, pyrimidinyl, oxazolyl, isoxazolyl, pyrazolyl, imidazolyl, thiazolyl, isothiazolyl and the like. Fused polycyclic aryl groups are those aromatic groups that include a 5- or 6-membered aromatic or heteroaromatic ring as one or more rings in a fused ring system. Representative fused polycyclic aryl groups include naphthalene, anthracene, indolizine, indole, isoindole, benzofuran, benzothiophene, indazole, benzimidazole, benzthiazole, purine, quinoline, isoquinoline, cinnoline, phthalazine, quinazoline, quinoxaline, 1,8-naphthyridine, pteridine, carbazole, acridine, phenazine, phenothiazine, phenoxazine, and azulene.

As used herein, a "carbonyl group-containing moiety" is a moiety of the formula —X—C(=Y)—Z—Ar, where X, C, Y, Z and Ar are as defined herein.

As used herein, "Cy" groups are 5- and 6-membered ring heteroaromatic groups. Representative Cy groups include pyridinyl, pyrimidinyl, furanyl, pyrrolyl, thienyl, oxazolyl, isoxazolyl, pyrazolyl, imidazolyl, thiazolyl, isothiazolyl and the like.

Individually, Ar and Cy can be unsubstituted or can be substituted with 1, 2 or 3 substituents, such as alkyl, alkenyl, heterocyclyl, cycloalkyl, aryl, substituted aryl, arylalkyl, substituted arylalkyl, halo (e.g., F, Cl, Br, or I), —OR', —NR'R", —CF$_3$, —CN, —NO$_2$, —C$_2$R', —SR', —N$_3$, —C(=O)NR'R", —NR'C(=O)R", —C(=O)R', —C(=O)OR', —OC(=O)R', —O(CR'R")$_r$C(=O)R', —O(CR'R")$_r$NR"C(=O)R', —O(CR'R")$_r$NR"SO$_2$R', —OC(=O)NR'R", —NR'C(=O)OR", —SO$_2$R', —SO$_2$NR'R", and —NR'SO$_2$R", where R' and R" are individually hydrogen, lower alkyl (e.g., straight chain or branched alkyl including C$_1$-C$_8$, preferably C$_1$-C$_5$, such as methyl, ethyl, or isopropyl), cycloalkyl, heterocyclyl, aryl, or arylalkyl (such as benzyl), and r is an integer from 1 to 6. R' and R" can also combine to form a cyclic functionality.

As used herein, cycloalkyl radicals contain from 3 to 8 carbon atoms. Examples of suitable cycloalkyl radicals include, but are not limited to, cyclopropyl, cyclobutyl, cyclopentyl, cyclohexyl, cycloheptyl and cyclooctyl. As used herein, polycycloalkyl radicals are selected from adamantyl, bornanyl, norbornanyl, bornenyl and norbornenyl.

As used herein, halogen is chlorine, iodine, fluorine or bromine.

As used herein, heteroaryl radicals are rings that contain from 3 to 10 members, preferably 5 or 6 members, including one or more heteroatoms selected from oxygen, sulphur and nitrogen. Examples of suitable 5-membered ring heteroaryl moieties include furyl, pyrrolyl, imidazolyl, oxazolyl, thiazolyl, thienyl, tetrazolyl, and pyrazolyl. Examples of suitable 6-membered ring heteroaryl moieties include pyridinyl, pyrimidinyl, pyrazinyl, of which pyridinyl and pyrimidinyl are preferred.

As used herein, "heterocyclic" or "heterocyclyl" radicals include rings with 3 to 10 members, including one or more heteroatoms selected from oxygen, sulphur and nitrogen. Examples of suitable heterocyclic moieties include, but are not limited to, piperidinyl, morpholinyl, pyrrolidinyl, imidazolidinyl, pyrazolidinyl, isothiazolidinyl, thiazolidinyl, isoxazolidinyl, oxazolidinyl, piperazinyl, tetrahydropyranyl and tetrahydrofuranyl.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. Representative salts are provided as described in U.S. Pat. No. 5,597,919 to Dull et al., U.S. Pat. No. 5,616,716 to Dull et al. and U.S. Pat. No. 5,663,356 to Ruecroft et al.

As used herein, neurotransmitters whose release is modulated (i.e., increased or decreased, depending on whether the compounds function as agonists, partial agonists or antagonists) by the compounds described herein include, but are not limited to, acetylcholine, dopamine, norepinephrine, serotonin and glutamate, and the compounds described herein function as modulators of one or more nicotinic receptors.

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to an decrease in a particular effect or function that is induced by interaction of the antagonist with a binding partner, and can include allosteric effects.

As used herein, a "partial agonist" is a substance that provides a level of stimulation to its binding partner that is intermediate between that of a full or complete antagonist and an agonist defined by any accepted standard for agonist activity. It will be recognized that stimulation, and hence, inhibition is defined intrinsically for any substance or category of substances to be defined as agonists, antagonists, or partial agonists. As used herein, "intrinsic activity", or "efficacy," relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. See Hoyer, D. and Boddeke, H., *Trends Pharmacol Sci.* 14(7):270-5 (1993). Where such contextually specific evaluations are relevant, and how they might be relevant in the context of the present invention, will be apparent to one of ordinary skill in the art.

In one embodiment, the value of p is 1, Cy is 3-pyridinyl or 5-pyrimidinyl, X and Y are oxygen, Z is nitrogen and the relative stereochemistry of the substituents in the 2 and 3 positions of the azabicycle is cis. In another embodiment, the value of p is 1, Cy is 3-pyridinyl or 5-pyrimidinyl, X and Z are nitrogen, Y is oxygen, and the relative stereochemistry of the substituents in the 2 and 3 positions of the azabicycle is cis. In a third embodiment, the value of p is 1, Cy is 3-pyridinyl or 5-pyrimidinyl, X is nitrogen, Y is oxygen, Z is a covalent bond (between the carbonyl and Ar) and the relative stereochemistry of the substituents in the 2 and 3 positions of the azabicycle is cis. In a fourth embodiment, the value of p is 1, Cy is 3-pyridinyl or 5-pyrimidinyl, X is nitrogen, Y is oxygen, Z is A (a linker species between the carbonyl and Ar) and the relative stereochemistry of the substituents in the 2 and 3 positions of the azabicycle is cis.

Representative compounds of the present invention include:

(R,R; R,S; S,R; and S,S)-2-((3-pyridinyl)methyl)-1-azabicyclo[2.2.2]oct-3-yl N-phenylcarbamate,
(R,R; R,S; S,R; and S,S)-2-((3-pyridinyl)methyl)-1-azabicyclo[2.2.2]oct-3-yl N-(4-fluorophenyl)carbamate,
(R,R; R,S; S,R; and S,S)-2-((3-pyridinyl)methyl)-1-azabicyclo[2.2.2]oct-3-yl N-(4-chlorophenyl)carbamate,
(R,R; R,S; S,R; and S,S)-2-((3-pyridinyl)methyl)-1-azabicyclo[2.2.2]oct-3-yl N-(4-bromophenyl)carbamate,
(R,R; R,S; S,R; and S,S)-2-((3-pyridinyl)methyl)-1-azabicyclo[2.2.2]oct-3-yl N-(3-fluorophenyl)carbamate,
(R,R; R,S; S,R; and S,S)-2-((3-pyridinyl)methyl)-1-azabicyclo[2.2.2]oct-3-yl N-(3-chlorophenyl)carbamate,
(R,R; R,S; S,R; and S,S)-2-((3-pyridinyl)methyl)-1-azabicyclo[2.2.2]oct-3-yl N-(3-bromophenyl)carbamate,
(R,R; R,S; S,R; and S,S)-2-((3-pyridinyl)methyl)-1-azabicyclo[2.2.2]oct-3-yl N-(2-fluorophenyl)carbamate,
(R,R; R,S; S,R; and S,S)-2-((3-pyridinyl)methyl)-1-azabicyclo[2.2.2]oct-3-yl N-(2-chlorophenyl)carbamate,
(R,R; R,S; S,R; and S,S)-2-((3-pyridinyl)methyl)-1-azabicyclo[2.2.2]oct-3-yl N-(2-bromophenyl)carbamate,
(R,R; R,S; S,R; and S,S)-2-((3-pyridinyl)methyl)-1-azabicyclo[2.2.2]oct-3-yl N-(3,4-dichlorophenyl)carbamate,
(R,R; R,S; S,R; and S,S)-2-((3-pyridinyl)methyl)-1-azabicyclo[2.2.2]oct-3-yl N-(2-methylphenyl)carbamate,
(R,R; R,S; S,R; and S,S)-2-((3-pyridinyl)methyl)-1-azabicyclo[2.2.2]oct-3-yl N-(2-biphenyl)carbamate,
(R,R; R,S; S,R; and S,S)-2-((3-pyridinyl)methyl)-1-azabicyclo[2.2.2]oct-3-yl N-(3-methylphenyl)carbamate,
(R,R; R,S; S,R; and S,S)-2-((3-pyridinyl)methyl)-1-azabicyclo[2.2.2]oct-3-yl N-(3-biphenyl)carbamate,
(R,R; R,S; S,R; and S,S)-2-((3-pyridinyl)methyl)-1-azabicyclo[2.2.2]oct-3-yl N-(4-methylphenyl)carbamate,
(R,R; R,S; S,R; and S,S)-2-((3-pyridinyl)methyl)-1-azabicyclo[2.2.2]oct-3-yl N-(4-biphenyl)carbamate,
(R,R; R,S; S,R; and S,S)-2-((3-pyridinyl)methyl)-1-azabicyclo[2.2.2]oct-3-yl N-(2-cyanophenyl)carbamate,
(R,R; R,S; S,R; and S,S)-2-((3-pyridinyl)methyl)-1-azabicyclo[2.2.2]oct-3-yl N-(3-cyanophenyl)carbamate,
(R,R; R,S; S,R; and S,S)-2-((3-pyridinyl)methyl)-1-azabicyclo[2.2.2]oct-3-yl N-(4-cyanophenyl)carbamate,
(R,R; R,S; S,R; and S,S)-2-((3-pyridinyl)methyl)-1-azabicyclo[2.2.2]oct-3-yl N-(3-trifluoromethylphenyl)carbamate,
(R,R; R,S; S,R; and S,S)-2-((3-pyridinyl)methyl)-1-azabicyclo[2.2.2]oct-3-yl N-(4-dimethylaminophenyl)carbamate,
(R,R; R,S; S,R; and S,S)-2-((3-pyridinyl)methyl)-1-azabicyclo[2.2.2]oct-3-yl N-(2-methoxyphenyl)carbamate,
(R,R; R,S; S,R; and S,S)-2-((3-pyridinyl)methyl)-1-azabicyclo[2.2.2]oct-3-yl N-(2-phenoxyphenyl)carbamate, (R,R; R,S; S,R; and S,S)-2-((3-pyridinyl)methyl)-1-azabicyclo[2.2.2]oct-3-yl N-(2-methylthiophenyl)carbamate,
(R,R; R,S; S,R; and S,S)-2-((3-pyridinyl)methyl)-1-azabicyclo[2.2.2]oct-3-yl N-(2-phenylthiophenyl)carbamate,
(R,R; R,S; S,R; and S,S)-2-((3-pyridinyl)methyl)-1-azabicyclo[2.2.2]oct-3-yl N-(3-methoxyphenyl)carbamate,
(R,R; R,S; S,R; and S,S)-2-((3-pyridinyl)methyl)-1-azabicyclo[2.2.2]oct-3-yl N-(3-phenoxyphenyl)carbamate,
(R,R; R,S; S,R; and S,S)-2-((3-pyridinyl)methyl)-1-azabicyclo[2.2.2]oct-3-yl N-(3-methylthiophenyl)carbamate,
(R,R; R,S; S,R; and S,S)-2-((3-pyridinyl)methyl)-1-azabicyclo[2.2.2]oct-3-yl N-(3-phenylthiophenyl)carbamate,
(R,R; R,S; S,R; and S,S)-2-((3-pyridinyl)methyl)-1-azabicyclo[2.2.2]oct-3-yl N-(4-methoxyphenyl)carbamate,
(R,R; R,S; S,R; and S,S)-2-((3-pyridinyl)methyl)-1-azabicyclo[2.2.2]oct-3-yl N-(4-phenoxyphenyl)carbamate,
(R,R; R,S; S,R; and S,S)-2-((3-pyridinyl)methyl)-1-azabicyclo[2.2.2]oct-3-yl N-(4-methylthiophenyl)carbamate,
(R,R; R,S; S,R; and S,S)-2-((3-pyridinyl)methyl)-1-azabicyclo[2.2.2]oct-3-yl N-(4-phenylthiophenyl)carbamate,
(R,R; R,S; S,R; and S,S)-2-((3-pyridinyl)methyl)-1-azabicyclo[2.2.2]oct-3-yl N-(2,4-dimethoxyphenyl)carbamate,
(R,R; R,S; S,R; and S,S)-2-((3-pyridinyl)methyl)-1-azabicyclo[2.2.2]oct-3-yl N-(2-thienyl)carbamate,
(R,R; R,S; S,R; and S,S)-2-((3-pyridinyl)methyl)-1-azabicyclo[2.2.2]oct-3-yl N-(3-thienyl)carbamate,
(R,R; R,S; S,R; and S,S)-2-((3-pyridinyl)methyl)-1-azabicyclo[2.2.2]oct-3-yl N-(3-benzothienyl)carbamate,
(R,R; R,S; S,R; and S,S)-2-((3-pyridinyl)methyl)-1-azabicyclo[2.2.2]oct-3-yl N-(1-naphthyl)carbamate, and
(R,R; R,S; S,R; and S,S)-2-((3-pyridinyl)methyl)-1-azabicyclo[2.2.2]oct-3-yl N-(2-naphthyl)carbamate.

Other compounds representative of the present invention include:
(R,R; R,S; S,R; and S,S)—N-phenyl-N'-(2-((3-pyridinyl)methyl)-1-azabicyclo[2.2.2]oct-3-yl)urea,
(R,R; R,S; S,R; and S,S)—N-(4-fluorophenyl)-N'-(2-((3-pyridinyl)methyl)-1-azabicyclo[2.2.2]oct-3-yl)urea,
(R,R; R,S; S,R; and S,S)—N-(4-chlorophenyl)-N'-(2-((3-pyridinyl)methyl)-1-azabicyclo[2.2.2]oct-3-yl)urea,
(R,R; R,S; S,R; and S,S)—N-(4-bromophenyl)-N'-(2-((3-pyridinyl)methyl)-1-azabicyclo[2.2.2]oct-3-yl)urea,
(R,R; R,S; S,R; and S,S)—N-(3-fluorophenyl)-N'-(2-((3-pyridinyl)methyl)-1-azabicyclo[2.2.2]oct-3-yl)urea,
(R,R; R,S; S,R; and S,S)—N-(3-chlorophenyl)-N'-(2-((3-pyridinyl)methyl)-1-azabicyclo[2.2.2]oct-3-yl)urea,
(R,R; R,S; S,R; and S,S)—N-(3-bromophenyl)-N'-(2-((3-pyridinyl)methyl)-1-azabicyclo[2.2.2]oct-3-yl)urea,
(R,R; R,S; S,R; and S,S)—N-(2-fluorophenyl)-N'-(2-((3-pyridinyl)methyl)-1-azabicyclo[2.2.2]oct-3-yl)urea,
(R,R; R,S; S,R; and S,S)—N-(2-chlorophenyl)-N'-(2-((3-pyridinyl)methyl)-1-azabicyclo[2.2.2]oct-3-yl)urea,
(R,R; R,S; S,R; and S,S)—N-(2-bromophenyl)-N'-(2-((3-pyridinyl)methyl)-1-azabicyclo[2.2.2]oct-3-yl)urea,
(R,R; R,S; S,R; and S,S)—N-(3,4-dichlorophenyl)-N'-(2-((3-pyridinyl)methyl)-1-azabicyclo[2.2.2]oct-3-yl)urea,
(R,R; R,S; S,R; and S,S)—N-(2-methylphenyl)-N'-(2-((3-pyridinyl)methyl)-1-azabicyclo[2.2.2]oct-3-yl)urea,
(R,R; R,S; S,R; and S,S)—N-(2-biphenyl)-N'-(2-((3-pyridinyl)methyl)-1-azabicyclo[2.2.2]oct-3-yl)urea,
(R,R; R,S; S,R; and S,S)—N-(3-methylphenyl)-N'-(2-((3-pyridinyl)methyl)-1-azabicyclo[2.2.2]oct-3-yl)urea,
(R,R; R,S; S,R; and S,S)—N-(3-biphenyl)-N'-(2-((3-pyridinyl)methyl)-1-azabicyclo[2.2.2]oct-3-yl)urea,
(R,R; R,S; S,R; and S,S)—N-(4-methylphenyl)-N'-(2-((3-pyridinyl)methyl)-1-azabicyclo[2.2.2]oct-3-yl)urea,
(R,R; R,S; S,R; and S,S)—N-(4-biphenyl)-N-(2-((3-pyridinyl)methyl)-1-azabicyclo[2.2.2]oct-3-yl)urea,
(R,R; R,S; S,R; and S,S)—N-(2-cyanophenyl)-N'-(2-((3-pyridinyl)methyl)-1-azabicyclo[2.2.2]oct-3-yl)urea,
(R,R; R,S; S,R; and S,S)—N-(3-cyanophenyl)-N'-(2-((3-pyridinyl)methyl)-1-azabicyclo[2.2.2]oct-3-yl)urea,
(R,R; R,S; S,R; and S,S)—N-(4-cyanophenyl)-N'-(2-((3-pyridinyl)methyl)-1-azabicyclo[2.2.2]oct-3-yl)urea,
(R,R; R,S; S,R; and S,S)—N-(3-trifluoromethylphenyl)-N'-(2-((3-pyridinyl)methyl)-1-azabicyclo[2.2.2]oct-3-yl)urea,
(R,R; R,S; S,R; and S,S)—N-(4-dimethylaminophenyl)-N'-(2-((3-pyridinyl)methyl)-1-azabicyclo[2.2.2]oct-3-yl)urea,
(R,R; R,S; S,R; and S,S)—N-(2-methoxyphenyl)-N'-(2-((3-pyridinyl)methyl)-1-azabicyclo[2.2.2]oct-3-yl)urea,
(R,R; R,S; S,R; and S,S)—N-(2-phenoxyphenyl)-N'-(2-((3-pyridinyl)methyl)-1-azabicyclo[2.2.2]oct-3-yl)urea,
(R,R; R,S; S,R; and S,S)—N-(2-methylthiophenyl)-N'-(2-((3-pyridinyl)methyl)-1-azabicyclo[2.2.2]oct-3-yl)urea,
(R,R; R,S; S,R; and S,S)—N-(2-phenylthiophenyl)-N'-(2-((3-pyridinyl)methyl)-1-azabicyclo[2.2.2]oct-3-yl)urea,
(R,R; R,S; S,R; and S,S)—N-(3-methoxyphenyl)-N'-(2-((3-pyridinyl)methyl)-1-azabicyclo[2.2.2]oct-3-yl)urea,
(R,R; R,S; S,R; and S,S)—N-(3-phenoxyphenyl)-N'-(2-((3-pyridinyl)methyl)-1-azabicyclo[2.2.2]oct-3-yl)urea,
(R,R; R,S; S,R; and S,S)—N-(3-methylthiophenyl)-N'-(2-((3-pyridinyl)methyl)-1-azabicyclo[2.2.2]oct-3-yl)urea,
(R,R; R,S; S,R; and S,S)—N-(3-phenylthiophenyl)-N'-(2-((3-pyridinyl)methyl)-1-azabicyclo[2.2.2]oct-3-yl)urea,
(R,R; R,S; S,R; and S,S)—N-(4-methoxyphenyl)-N'-(2-((3-pyridinyl)methyl)-1-azabicyclo[2.2.2]oct-3-yl)urea,
(R,R; R,S; S,R; and S,S)—N-(4-phenoxyphenyl)-N'-(2-((3-pyridinyl)methyl)-1-azabicyclo[2.2.2]oct-3-yl)urea,
(R,R; R,S; S,R; and S,S)—N-(4-methylthiophenyl)-N'-(2-((3-pyridinyl)methyl)-1-azabicyclo[2.2.2]oct-3-yl)urea,
(R,R; R,S; S,R; and S,S)—N-(4-phenylthiophenyl)-N'-(2-((3-pyridinyl)methyl)-1-azabicyclo[2.2.2]oct-3-yl)urea,
(R,R; R,S; S,R; and S,S)—N-(2,4-dimethoxyphenyl)-N'-(2-((3-pyridinyl)methyl)-1-azabicyclo[2.2.2]oct-3-yl)urea,
(R,R; R,S; S,R; and S,S)—N-(2-thienyl)-N'-(2-((3-pyridinyl)methyl)-1-azabicyclo[2.2.2]oct-3-yl)urea,
(R,R; R,S; S,R; and S,S)—N-(3-thienyl)-N'-(2-((3-pyridinyl)methyl)-1-azabicyclo[2.2.2]oct-3-yl)urea,
(R,R; R,S; S,R; and S,S)—N-(3-benzothienyl)-N'-(2-((3-pyridinyl)methyl)-1-azabicyclo[2.2.2]oct-3-yl)urea,
(R,R; R,S; S,R; and S,S)—N-(1-naphthyl)-N'-(2-((3-pyridinyl)methyl)-1-azabicyclo[2.2.2]oct-3-yl)urea, and
(R,R; R,S; S,R; and S,S)—N-(2-naphthyl)-N'-(2-((3-pyridinyl)methyl)-1-azabicyclo[2.2.2]oct-3-yl)urea.

Other compounds representative of the present invention include:
(R,R; R,S; S,R; and S,S)—N-(2-((3-pyridinyl)methyl)-1-azabicyclo[2.2.2]oct-3-yl)benzamide,
(R,R; R,S; S,R; and S,S)—N-(2-((3-pyridinyl)methyl)-1-azabicyclo[2.2.2]oct-3-yl)-2-fluorobenzamide,
(R,R; R,S; S,R; and S,S)—N-(2-((3-pyridinyl)methyl)-1-azabicyclo[2.2.2]oct-3-yl)-3-fluorobenzamide,
(R,R; R,S; S,R; and S,S)—N-(2-((3-pyridinyl)methyl)-1-azabicyclo[2.2.2]oct-3-yl)-4-fluorobenzamide,
(R,R; R,S; S,R; and S,S)—N-(2-((3-pyridinyl)methyl)-1-azabicyclo[2.2.2]oct-3-yl)-2-chlorobenzamide,
(R,R; R,S; S,R; and S,S)—N-(2-((3-pyridinyl)methyl)-1-azabicyclo[2.2.2]oct-3-yl)-3-chlorobenzamide,
(R,R; R,S; S,R; and S,S)—N-(2-((3-pyridinyl)methyl)-1-azabicyclo[2.2.2]oct-3-yl)-4-chlorobenzamide, (R,R; R,S; S,R; and S,S)—N-(2-((3-pyridinyl)methyl)-1-azabicyclo[2.2.2]oct-3-yl)-2-bromobenzamide,
(R,R; R,S; S,R; and S,S)—N-(2-((3-pyridinyl)methyl)-1-azabicyclo[2.2.2]oct-3-yl)-3-bromobenzamide,
(R,R; R,S; S,R; and S,S)—N-(2-((3-pyridinyl)methyl)-1-azabicyclo[2.2.2]oct-3-yl)-4-bromobenzamide,
(R,R; R,S; S,R; and S,S)—N-(2-((3-pyridinyl)methyl)-1-azabicyclo[2.2.2]oct-3-yl)-3,4-dichlorobenzamide,
(R,R; R,S; S,R; and S,S)—N-(2-((3-pyridinyl)methyl)-1-azabicyclo[2.2.2]oct-3-yl)-2-methylbenzamide,
(R,R; R,S; S,R; and S,S)—N-(2-((3-pyridinyl)methyl)-1-azabicyclo[2.2.2]oct-3-yl)-3-methylbenzamide,
(R,R; R,S; S,R; and S,S)—N-(2-((3-pyridinyl)methyl)-1-azabicyclo[2.2.2]oct-3-yl)-4-methylbenzamide,
(R,R; R,S; S,R; and S,S)—N-(2-((3-pyridinyl)methyl)-1-azabicyclo[2.2.2]oct-3-yl)-2-phenylbenzamide,
(R,R; R,S; S,R; and S,S)—N-(2-((3-pyridinyl)methyl)-1-azabicyclo[2.2.2]oct-3-yl)-3-phenylbenzamide,
(R,R; R,S; S,R; and S,S)—N-(2-((3-pyridinyl)methyl)-1-azabicyclo[2.2.2]oct-3-yl)-4-phenylbenzamide,
(R,R; R,S; S,R; and S,S)—N-(2-((3-pyridinyl)methyl)-1-azabicyclo[2.2.2]oct-3-yl)-2-cyanobenzamide,
(R,R; R,S; S,R; and S,S)—N-(2-((3-pyridinyl)methyl)-1-azabicyclo[2.2.2]oct-3-yl)-3-cyanobenzamide,
(R,R; R,S; S,R; and S,S)—N-(2-((3-pyridinyl)methyl)-1-azabicyclo[2.2.2]oct-3-yl)-4-cyanobenzamide,
(R,R; R,S; S,R; and S,S)—N-(2-((3-pyridinyl)methyl)-1-azabicyclo[2.2.2]oct-3-yl)-3-trifluoromethylbenzamide,
(R,R; R,S; S,R; and S,S)—N-(2-((3-pyridinyl)methyl)-1-azabicyclo[2.2.2]oct-3-yl)-4-dimethylaminobenzamide,
(R,R; R,S; S,R; and S,S)—N-(2-((3-pyridinyl)methyl)-1-azabicyclo[2.2.2]oct-3-yl)-2-methoxybenzamide,
(R,R; R,S; S,R; and S,S)—N-(2-((3-pyridinyl)methyl)-1-azabicyclo[2.2.2]oct-3-yl)-3-methoxybenzamide,
(R,R; R,S; S,R; and S,S)—N-(2-((3-pyridinyl)methyl)-1-azabicyclo[2.2.2]oct-3-yl)-4-methoxybenzamide,
(R,R; R,S; S,R; and S,S)—N-(2-((3-pyridinyl)methyl)-1-azabicyclo[2.2.2]oct-3-yl)-2-phenoxybenzamide,
(R,R; R,S; S,R; and S,S)—N-(2-((3-pyridinyl)methyl)-1-azabicyclo[2.2.2]oct-3-yl)-3-phenoxybenzamide,
(R,R; R,S; S,R; and S,S)—N-(2-((3-pyridinyl)methyl)-1-azabicyclo[2.2.2]oct-3-yl)-4-phenoxybenzamide,
(R,R; R,S; S,R; and S,S)—N-(2-((3-pyridinyl)methyl)-1-azabicyclo[2.2.2]oct-3-yl)-2-methylthiobenzamide,
(R,R; R,S; S,R; and S,S)—N-(2-((3-pyridinyl)methyl)-1-azabicyclo[2.2.2]oct-3-yl)-3-methylthiobenzamide,
(R,R; R,S; S,R; and S,S)—N-(2-((3-pyridinyl)methyl)-1-azabicyclo[2.2.2]oct-3-yl)-4-methylthiobenzamide,
(R,R; R,S; S,R; and S,S)—N-(2-((3-pyridinyl)methyl)-1-azabicyclo[2.2.2]oct-3-yl)-2-phenylthiobenzamide,
(R,R; R,S; S,R; and S,S)—N-(2-((3-pyridinyl)methyl)-1-azabicyclo[2.2.2]oct-3-yl)-3-phenylthiobenzamide,
(R,R; R,S; S,R; and S,S)—N-(2-((3-pyridinyl)methyl)-1-azabicyclo[2.2.2]oct-3-yl)-4-phenylthiobenzamide,
(R,R; R,S; S,R; and S,S)—N-(2-((3-pyridinyl)methyl)-1-azabicyclo[2.2.2]oct-3-yl)-2,4-dimethoxybenzamide,
(R,R; R,S; S,R; and S,S)—N-(2-((3-pyridinyl)methyl)-1-azabicyclo[2.2.2]oct-3-yl)-5-bromonicotinamide,
(R,R; R,S; S,R; and S,S)—N-(2-((3-pyridinyl)methyl)-1-azabicyclo[2.2.2]oct-3-yl)-6-chloronicotinamide,
(R,R; R,S; S,R; and S,S)—N-(2-((3-pyridinyl)methyl)-1-azabicyclo[2.2.2]oct-3-yl)-5-phenylnicotinamide,
(R,R; R,S; S,R; and S,S)—N-(2-((3-pyridinyl)methyl)-1-azabicyclo[2.2.2]oct-3-yl)furan-2-carboxamide,
(R,R; R,S; S,R; and S,S)—N-(2-((3-pyridinyl)methyl)-1-azabicyclo[2.2.2]oct-3-yl)furan-3-carboxamide,
(R,R; R,S; S,R; and S,S)—N-(2-((3-pyridinyl)methyl)-1-azabicyclo[2.2.2]oct-3-yl)thiophene-2-carboxamide,
(R,R; R,S; S,R; and S,S)—N-(2-((3-pyridinyl)methyl)-1-azabicyclo[2.2.2]oct-3-yl)-5-bromothiophene-2-carboxamide,
(R,R; R,S; S,R; and S,S)—N-(2-((3-pyridinyl)methyl)-1-azabicyclo[2.2.2]oct-3-yl)-5-methylthiothiophene-2-carboxamide,
(R,R; R,S; S,R; and S,S)—N-(2-((3-pyridinyl)methyl)-1-azabicyclo[2.2.2]oct-3-yl)-5-phenylthiothiophene-2-carboxamide,
(R,R; R,S; S,R; and S,S)—N-(2-((3-pyridinyl)methyl)-1-azabicyclo[2.2.2]oct-3-yl)-5-methylthiophene-2-carboxamide,
(R,R; R,S; S,R; and S,S)—N-(2-((3-pyridinyl)methyl)-1-azabicyclo[2.2.2]oct-3-yl)-3-methylthiophene-2-carboxamide,
(R,R; R,S; S,R; and S,S)—N-(2-((3-pyridinyl)methyl)-1-azabicyclo[2.2.2]oct-3-yl)-3-bromothiophene-2-carboxamide,
(R,R; R,S; S,R; and S,S)—N-(2-((3-pyridinyl)methyl)-1-azabicyclo[2.2.2]oct-3-yl)-3-chlorothiophene-2-carboxamide,
(R,R; R,S; S,R; and S,S)—N-(2-((3-pyridinyl)methyl)-1-azabicyclo[2.2.2]oct-3-yl)-5-(2-pyridinyl)thiophene-2-carboxamide,
(R,R; R,S; S,R; and S,S)—N-(2-((3-pyridinyl)methyl)-1-azabicyclo[2.2.2]oct-3-yl)-5-acetylthiophene-2-carboxamide,
(R,R; R,S; S,R; and S,S)—N-(2-((3-pyridinyl)methyl)-1-azabicyclo[2.2.2]oct-3-yl)-3-ethoxythiophene-2-carboxamide,
(R,R; R,S; S,R; and S,S)—N-(2-((3-pyridinyl)methyl)-1-azabicyclo[2.2.2]oct-3-yl)-3-methoxythiophene-2-carboxamide,
(R,R; R,S; S,R; and S,S)—N-(2-((3-pyridinyl)methyl)-1-azabicyclo[2.2.2]oct-3-yl)-4-acetyl-3-methyl-5-methylthiothiophene-2-carboxamide,
(R,R; R,S; S,R; and S,S)—N-(2-((3-pyridinyl)methyl)-1-azabicyclo[2.2.2]oct-3-yl)thiophene-3-carboxamide,
(R,R; R,S; S,R; and S,S)—N-(2-((3-pyridinyl)methyl)-1-azabicyclo[2.2.2]oct-3-yl)-1-methylpyrrole-2-carboxamide,
(R,R; R,S; S,R; and S,S)—N-(2-((3-pyridinyl)methyl)-1-azabicyclo[2.2.2]oct-3-yl)pyrrole-3-carboxamide,
(R,R; R,S; S,R; and S,S)—N-(2-((3-pyridinyl)methyl)-1-azabicyclo[2.2.2]oct-3-yl)indole-2-carboxamide,
(R,R; R,S; S,R; and S,S)—N-(2-((3-pyridinyl)methyl)-1-azabicyclo[2.2.2]oct-3-yl)indole-3-carboxamide,
(R,R; R,S; S,R; and S,S)—N-(2-((3-pyridinyl)methyl)-1-azabicyclo[2.2.2]oct-3-yl)-1-methylindole-3-carboxamide,
(R,R; R,S; S,R; and S,S)—N-(2-((3-pyridinyl)methyl)-1-azabicyclo[2.2.2]oct-3-yl)-1-benzylindole-3-carboxamide,
(R,R; R,S; S,R; and S,S)—N-(2-((3-pyridinyl)methyl)-1-azabicyclo[2.2.2]oct-3-yl)-1H-benzimidazole-2-carboxamide,
(R,R; R,S; S,R; and S,S)—N-(2-((3-pyridinyl)methyl)-1-azabicyclo[2.2.2]oct-3-yl)-1-isopropyl-2-trifluoromethyl-1H-benzimidazole-5-carboxamide,
(R,R; R,S; S,R; and S,S)—N-(2-((3-pyridinyl)methyl)-1-azabicyclo[2.2.2]oct-3-yl)-1-isopropyl-1H-benzotriazole-5-carboxamide,
(R,R; R,S; S,R; and S,S)—N-(2-((3-pyridinyl)methyl)-1-azabicyclo[2.2.2]oct-3-yl)benzo[b]thiophene-2-carboxamide, (R,R; R,S; S,R; and S,S)—N-(2-((3-pyridinyl)methyl)-1-azabicyclo[2.2.2]oct-3-yl)benzo[b]thiophene-3-carboxamide,
(R,R; R,S; S,R; and S,S)—N-(2-((3-pyridinyl)methyl)-1-azabicyclo[2.2.2]oct-3-yl)benzofuran-2-carboxamide,
(R,R; R,S; S,R; and S,S)—N-(2-((3-pyridinyl)methyl)-1-azabicyclo[2.2.2]oct-3-yl)benzofuran-3-carboxamide,
(R,R; R,S; S,R; and S,S)—N-(2-((3-pyridinyl)methyl-1-azabicyclo[2.2.2]oct-3-yl)-3-methylbenzofuran-2-carboxamide,
(R,R; R,S; S,R; and S,S)—N-(2-((3-pyridinyl)methyl)-1-azabicyclo[2.2.2]oct-3-yl)-5-nitrobenzofuran-2-carboxamide,
(R,R; R,S; S,R; and S,S)—N-(2-((3-pyridinyl)methyl)-1-azabicyclo[2.2.2]oct-3-yl)-5-methoxybenzofuran-2-carboxamide,
(R,R; R,S; S,R; and S,S)—N-(2-((3-pyridinyl)methyl)-1-azabicyclo[2.2.2]oct-3-yl)-7-methoxybenzofuran-2-carboxamide,
(R,R; R,S; S,R; and S,S)—N-(2-((3-pyridinyl)methyl-1-azabicyclo[2.2.2]oct-3-yl)-7-ethoxybenzofuran-2-carboxamide,
(R,R; R,S; S,R; and S,S)—N-(2-((3-pyridinyl)methyl)-1-azabicyclo[2.2.2]oct-3-yl)-3-methyl-5-chlorobenzofuran-2-carboxamide,
(R,R; R,S; S,R; and S,S)—N-(2-((3-pyridinyl)methyl)-1-azabicyclo[2.2.2]oct-3-yl)-6-bromobenzofuran-2-carboxamide,
(R,R; R,S; S,R; and S,S)—N-(2-((3-pyridinyl)methyl)-1-azabicyclo[2.2.2]oct-3-yl)-4-acetyl-7-methoxybenzofuran-2-carboxamide,
(R,R; R,S; S,R; and S,S)—N-(2-((3-pyridinyl)methyl)-1-azabicyclo[2.2.2]oct-3-yl)-2-methylbenzofuran-4-carboxamide,
(R,R; R,S; S,R; and S,S)—N-(2-((3-pyridinyl)methyl)-1-azabicyclo[2.2.2]oct-3-yl)naphtho[2,1-b]furan-2-carboxamide,
(R,R; R,S; S,R; and S,S)—N-(2-((3-pyridinyl)methyl)-1-azabicyclo[2.2.2]oct-3-yl)naphthalene-1-carboxamide,
(R,R; R,S; S,R; and S,S)—N-(2-((3-pyridinyl)methyl)-1-azabicyclo[2.2.2]oct-3-yl)naphthalene-2-carboxamide,
(R,R; R,S; S,R; and S,S)—N-(2-((3-pyridinyl)methyl)-1-azabicyclo[2.2.2]oct-3-yl)-6-aminonaphthalene-2-carboxamide,
(R,R; R,S; S,R; and S,S)—N-(2-((3-pyridinyl)methyl)-1-azabicyclo[2.2.2]oct-3-yl)-3-methoxynaphthalene-2-carboxamide,
(R,R; R,S; S,R; and S,S)—N-(2-((3-pyridinyl)methyl)-1-azabicyclo[2.2.2]oct-3-yl)-6-methoxynaphthalene-2-carboxamide,
(R,R; R,S; S,R; and S,S)—N-(2-((3-pyridinyl)methyl)-1-azabicyclo[2.2.2]oct-3-yl)-1-hydroxynaphthalene-2-carboxamide,
(R,R; R,S; S,R; and S,S)—N-(2-((3-pyridinyl)methyl)-1-azabicyclo[2.2.2]oct-3-yl)-6-hydroxynaphthalene-2-carboxamide,
(R,R; R,S; S,R; and S,S)—N-(2-((3-pyridinyl)methyl)-1-azabicyclo[2.2.2]oct-3-yl)-6-acetoxynaphthalene-2-carboxamide,
(R,R; R,S; S,R; and S,S)—N-(2-((3-pyridinyl)methyl)-1-azabicyclo[2.2.2]oct-3-yl)-phenylprop-2-enamide,
(R,R; R,S; S,R; and S,S)—N-(2-((3-pyridinyl)methyl)-1-azabicyclo[2.2.2]oct-3-yl)-3-(3-fluorophenyl)prop-2-enamide,
(R,R; R,S; S,R; and S,S)—N-(2-((3-pyridinyl)methyl)-1-azabicyclo[2.2.2]oct-3-yl)-3-(4-methoxyphenyl)prop-2-enamide,
(R,R; R,S; S,R; and S,S)—N-(2-((3-pyridinyl)methyl)-1-azabicyclo[2.2.2]oct-3-yl)-2-methyl-3-phenylprop-2-enamide,
(R,R; R,S; S,R; and S,S)—N-(2-((3-pyridinyl)methyl)-1-azabicyclo[2.2.2]oct-3-yl)-3-(2-fluorophenyl)prop-2-enamide,
(R,R; R,S; S,R; and S,S)—N-(2-((3-pyridinyl)methyl)-1-azabicyclo[2.2.2]oct-3-yl)-3-(3-methylphenyl)prop-2-enamide,
(R,R; R,S; S,R; and S,S)—N-(2-((3-pyridinyl)methyl)-1-azabicyclo[2.2.2]oct-3-yl)-3-(4-fluorophenyl)prop-2-enamide,
(R,R; R,S; S,R; and S,S)—N-(2-((3-pyridinyl)methyl)-1-azabicyclo[2.2.2]oct-3-yl)-3-(4-methylphenyl)prop-2-enamide,
(R,R; R,S; S,R; and S,S)—N-(2-((3-pyridinyl)methyl)-1-azabicyclo[2.2.2]oct-3-yl)-3-(2-furyl)prop-2-enamide,
(R,R; R,S; S,R; and S,S)—N-(2-((3-pyridinyl)methyl)-1-azabicyclo[2.2.2]oct-3-yl)-3-(2-methoxyphenyl)prop-2-enamide,
(R,R; R,S; S,R; and S,S)—N-(2-((3-pyridinyl)methyl)-1-azabicyclo[2.2.2]oct-3-yl)-3-(3-bromophenyl)prop-2-enamide,
(R,R; R,S; S,R; and S,S)—N-(2-((3-pyridinyl)methyl)-1-azabicyclo[2.2.2]oct-3-yl)-3-(3-methoxyphenyl)prop-2-enamide,
(R,R; R,S; S,R; and S,S)—N-(2-((3-pyridinyl)methyl)-1-azabicyclo[2.2.2]oct-3-yl)-3-(3-hydroxyphenyl)prop-2-enamide,
(R,R; R,S; S,R; and S,S)—N-(2-((3-pyridinyl)methyl)-1-azabicyclo[2.2.2]oct-3-yl)-3-(4-bromophenyl)prop-2-enamide,
(R,R; R,S; S,R; and S,S)—N-(2-((3-pyridinyl)methyl)-1-azabicyclo[2.2.2]oct-3-yl)-3-(4-chlorophenyl)prop-2-enamide,
(R,R; R,S; S,R; and S,S)—N-(2-((3-pyridinyl)methyl)-1-azabicyclo[2.2.2]oct-3-yl)-3-(4-hydroxyphenyl)prop-2-enamide,
(R,R; R,S; S,R; and S,S)—N-(2-((3-pyridinyl)methyl)-1-azabicyclo[2.2.2]oct-3-yl)-3-(4-hydroxy-3-methoxyphenyl)prop-2-enamide,
(R,R; R,S; S,R; and S,S)—N-(2-((3-pyridinyl)methyl)-1-azabicyclo[2.2.2]oct-3-yl)-3-(2-thienyl)prop-2-enamide,
(R,R; R,S; S,R; and S,S)—N-(2-((3-pyridinyl)methyl)-1-azabicyclo[2.2.2]oct-3-yl)-3-(3-pyridinyl)prop-2-enamide,
(R,R; R,S; S,R; and S,S)—N-(2-((3-pyridinyl)methyl)-1-azabicyclo[2.2.2]oct-3-yl)-3-(4-biphenyl)prop-2-enamide,
(R,R; R,S; S,R; and S,S)—N-(2-((3-pyridinyl)methyl)-1-azabicyclo[2.2.2]oct-3-yl)-3-(1-naphthyl)prop-2-enamide,
(R,R; R,S; S,R; and S,S)—N-(2-((3-pyridinyl)methyl)-1-azabicyclo[2.2.2]oct-3-yl)-3-(3-thienyl)prop-2-enamide,
(R,R; R,S; S,R; and S,S)—N-(2-((3-pyridinyl)methyl)-1-azabicyclo[2.2.2]oct-3-yl)-3-(4-isopropylphenyl)prop-2-enamide,
(R,R; R,S; S,R; and S,S)—N-(2-((3-pyridinyl)methyl)-1-azabicyclo[2.2.2]oct-3-yl)-3-methyl-3-phenylprop-2-enamide,
(R,R; R,S; S,R; and S,S)—N-(2-((3-pyridinyl)methyl)-1-azabicyclo[2.2.2]oct-3-yl)-3-(3-furyl)prop-2-enamide,
(R,R; R,S; S,R; and S,S)—N-(2-((3-pyridinyl)methyl)-1-azabicyclo[2.2.2]oct-3-yl)-2-ethyl-3-phenylprop-2-enamide, (R,R; R,S; S,R; and S,S)—N-(2-((3-pyridinyl)methyl)-1-azabicyclo[2.2.2]oct-3-yl)-3-(2-pyridinyl)prop-2-enamide, (R,R; R,S; S,R; and S,S)—N-(2-((3-pyridinyl)methyl)-1-azabicyclo[2.2.2]oct-3-yl)-3-(3,4-dimethylthieno[2,3-b]thiophen-2-yl)prop-2-enamide, (R,R; R,S; S,R; and S,S)—N-(2-((3-pyridinyl)methyl)-1-azabicyclo[2.2.2]oct-3-yl)-3-(3-methylthien-2-yl)prop-2-enamide, (R,R; R,S; S,R; and S,S)—N-(2-((3-pyridinyl)methyl)-1-azabicyclo[2.2.2]oct-3-yl)-3-(2-naphthyl)prop-2-enamide, and (R,R; R,S; S,R; and S,S)—N-(2-((3-pyridinyl)methyl)-1-azabicyclo[2.2.2]oct-3-yl)-3-(4-methylthiophenyl)prop-2-enamide.

Compounds resulting from substitution of NCH$_3$ for NH, in any of the carbonyl group-containing moieties in the foregoing representative compounds, are also representative compounds of the present invention. Compounds resulting from the substitution of 1-azabicyclo[2.2.2]octane, in any of the forgoing representative compounds, with either 1-azabicyclo[2.2.1]heptane, 1-azabicyclo[3.2.1]octane or 1-azabicyclo[3.2.2]nonane are also representative compounds of the present invention.

More specifically, the compounds of Formula 2 include compounds of the following general formulas:

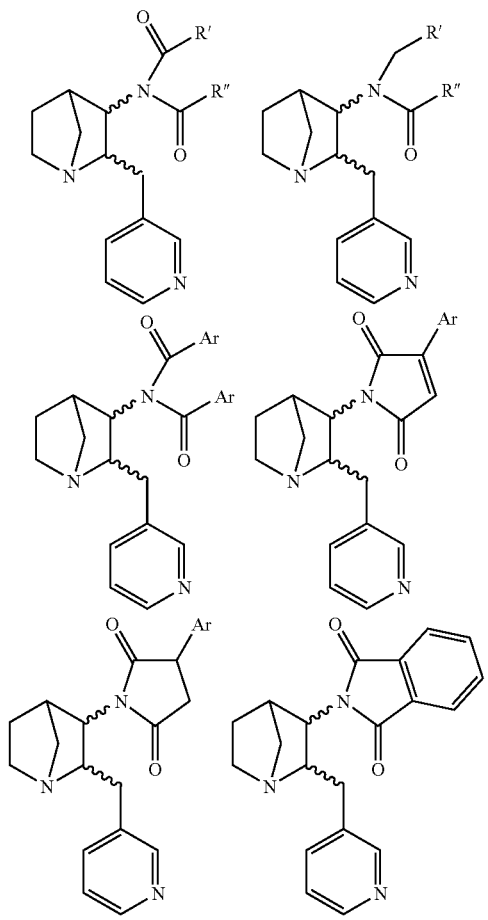

In each of these compounds, individual isomers thereof, mixtures thereof, including racemic mixtures, enantiomers, diastereomers and tautomers thereof, and the pharmaceutically acceptable salts thereof, are intended to be within the scope of the present invention.

I. Methods of Preparing the Compounds

Preparation of 2-(Arylalkyl)-1-azabicycloalkanes

Compounds of Formulas 1 and 2 are 3-substituted 2-(arylalkyl)-1-azabicycloalkanes. While the manner in which compounds of the present invention can be prepared can vary, they are conveniently prepared using intermediates (ketones and alcohols) generated during the synthesis of 2-(arylalkyl)-1-azabicycloalkanes, which is now described. While other synthetic strategies will be apparent to those of skill in the art, 2-(arylalkyl)-1-azabicycloalkanes can be made by reduction of aldol condensation products formed from aldehydes and certain azabicyclic ketones. Thus, when 3-quinuclidinone hydrochloride is reacted with pyridine-3-carboxaldehyde (available from Aldrich Chemical Company), in the presence of methanolic potassium hydroxide, 2-((3-pyridinyl)methylene)-1-azabicyclo[2.2.2]octan-3-one results. Stepwise reduction of the conjugated enone functionality can be accomplished through several different sequences, to provide 2-((3-pyridinyl)methyl)-1-azabicyclo[2.2.2]octane. For instance, catalytic hydrogenation (palladium catalyst) of the enone produces the saturated ketone, 2-((3-pyridinyl)methyl)-1-azabicyclo[2.2.2]octan-3-one, an intermediate in the synthesis of compounds of the present invention (see section entitled "Substituted-2-(Arylalkyl)-1-azabicycloalkanes"). Reduction of the ketone to the alcohol can be accomplished, for example, using sodium borohydride, aluminum isopropoxide, or other reagents known in the art of chemical synthesis for carrying out similar reductions. The alcohol, 2-((3-pyridinyl)methyl)-1-azabicyclo[2.2.2]octan-3-ol, is a mixture of cis and trans diastereomers (with the former predominating) and is also an intermediate in the synthesis of compounds of the present invention (see section entitled "Substituted-2-(Arylalkyl)-1-azabicycloalkanes"). The choice of reducing agent affects the cis/trans ratio. The alcohol can then be converted to the corresponding chloride, 3-chloro-2-((3-pyridinyl)methyl)-1-azabicyclo[2.2.2]octane, using thionyl chloride or similar reagents. The chloride can then be reduced to 2-((3-pyridinyl)methyl)-1-azabicyclo[2.2.2]octane, for example, using Raney nickel. The chloro intermediate can also be converted into the alkene, 2-((3-pyridinyl)methyl)-1-azabicyclo[2.2.2]oct-2-ene, which can then be reduced to the alkane by catalytic hydrogenation. 1,8-Diazabicyclo[5.4.0]undec-7-ene can be used for the dehydrohalogenation reaction, according to the method of Wolkoff, *J. Org. Chem.* 47: 1944 (1982). Alternatively, the 2-((3-pyridinyl)methylene)-1-azabicyclo[2.2.2]octan-3-one can then be converted into 2-((3-pyridinyl)methyl)-1-azabicyclo[2.2.2]octane by first reducing the ketone functionality using sodium borohydride. The resulting unsaturated alcohol, 2-((3-pyridinyl)methylene)-1-azabicyclo[2.2.2]octan-3-ol, is treated with thionyl chloride (to make the chloro compound), followed by Raney nickel (to reductively remove the chloro moiety), and then hydrogenated, for example, over a palladium catalyst (to reduce the double bond) to give the alkane. It is noteworthy that, when this latter route is employed, allylic rearrangements are observed. For instance, the material resulting from Raney nickel reduction of the chloro compound is a mixture of exocyclic and endocyclic alkenes, with the latter predominating. This route provides access to both 2-((3-pyridinyl)methylene)-1-azabicyclo[2.2.2]octane and 2-((3-pyridinyl)methyl)-1-azabicyclo[2.2.2]oct-2-ene.

In an alternative approach, 2-(arylalkyl)-1-azabicycloalkanes can be made by reacting aryl-containing organometallic compounds with azabicyclic carbonyl compounds and subsequently reducing the resulting alcohol, using the methods described above, to the alkane. For example, 2-((3-pyridinyl)hydroxymethyl)-1-azabicyclo[2.2.2]octane can be produced by reacting 3-pyridinyllithium with quinuclidine-2-carboxaldehyde. Reaction of the alcohol with thionyl chloride to produce the corresponding chloride, and subsequent reduction with Raney nickel, will give 2-((3-pyridinyl)methyl)-1-azabicyclo[2.2.2]octane. Synthesis of the requisite quinuclidine-2-carboxaldehyde is described by Ricciardi and Doukas, *Heterocycles* 24: 971 (1986), and the 3-pyridinyllithium can be generated from 3-bromopyridine by treatment with n-butyllithium in ether or toluene at low temperature (Cai et al., *Tetrahedron Lett.* 43: 4285 (2002)).

The manner in which 2-((4-, 5-, and 6-substituted-3-pyridinyl)methyl)-1-azabicyclo[2.2.2]octanes can be synthesized can vary. For example, 5-bromopyridine-3-carboxaldehyde and 3-quinuclidinone hydrochloride (commercially available from Aldrich) can be reacted together in the presence of methanolic potassium hydroxide as described in Neilsen and Houlihan, *Org. React.* 16: 1 (1968). The aldol condensation product, 2-((5-bromo-3-pyridinyl)methylene)-1-azabicyclo[2.2.2]octan-3-one, can then be treated with sodium borohydride to yield the alcohol, 2-((5-bromo-3-pyridinyl)methylene)-1-azabicyclo[2.2.2]octan-3-ol, as a crystalline solid. This intermediate is reacted with neat thionyl chloride at room temperature to give 3-chloro-2-(5-bromo-3-pyridinyl)methylene)-1-azabicyclo[2.2.2]octane dihydrochloride as a pure crystalline solid. Reductive removal of the chlorine can be accomplished using lithium trimethoxyaluminum hydride and copper iodide as described by Masamune et al., *J. Am. Chem. Soc.* 95: 6452 (1973) to give the desired product, 2-((5-bromo-3-pyridinyl)methylene)-1-azabicyclo[2.2.2]octane, as a crystalline solid. This methylene intermediate can then be converted to the desired product, 2-((5-bromo-3-pyridinyl)methyl)-1-azabicyclo[2.2.2]octane, by hydrogenation in the presence of palladium catalyst. The isomeric compounds, 2-((4-bromo-3-pyridinyl)methyl)-1-azabicyclo[2.2.2]octane and 2-((6-bromo-3-pyridinyl)methyl)-1-azabicyclo[2.2.2]octane can be prepared in a similar manner by replacing 5-bromopyridine-3-carboxaldehyde with 4-bromopyridine-3-carboxaldehyde or 6-bromopyridine-3-carboxaldehyde, respectively, in the synthetic approach given above.

The required aldehyde, 5-bromopyridine-3-carboxaldehyde, can be prepared from 5-bromonicotinic acid (commercially available from Aldrich Chemical Company and Lancaster Synthesis, Inc.). The 5-bromonicotinic acid can be treated with ethyl chloroformate to form a mixed anhydride, which can then be reduced, for example, with lithium aluminum hydride in tetrahydrofuran (THF) at −78° C., to afford 5-bromo-3-(hydroxymethyl)pyridine, as reported by Ashimori et al., *Chem. Pharm. Bull.* 38(9): 2446 (1990). Alternatively, the 5-bromonicotinic acid can be esterified, for example, in the presence of sulfuric acid and ethanol and the intermediate ethyl ester reduced with an excess of sodium borohydride to yield 5-bromo-3-(hydroxymethyl)pyridine, according to the techniques reported in Nutaitis et al., *Org. Prep. and Proc. Int* 24: 143 (1992). The resulting 5-bromo-3-(hydroxymethyl)pyridine can then be converted to 5-bromo-3-pyridinecarboxaldehyde by Swern oxidation using oxalyl chloride and dimethylsulfoxide, according to the methods of Stocks et al., *Tetrahedron Lett.* 36(36): 6555 (1995) and Mancuso et al., *J. Org. Chem.* 44(23): 4148 (1979). The aldehyde, 4-bromopyridine-3-carboxaldehyde can be synthesized according to methodology described in PCT WO 94/29893 by Chin et al. or by methodology described by Ojea et al., *Synlett.* 6: 622 (1995). 6-Bromopyridine-3-carboxaldehyde can be prepared according to procedures described in Windschief and Voegtle, *Synthesis* 1: 87 (1994) or German Patent No. 93/4320432 to Fey et al.

The methods described above are applicable to the preparation of a variety of 2-(arylmethyl)-1-azabicyclo[2.2.2]octanes, 2-(arylmethylene)-1-azabicyclo[2.2.2]octanes and 2-(arylmethyl)-1-azabicyclo[2.2.2]oct-2-enes by variation of the aldehyde component of the aldol condensation using no more than routine experimentation. Both substituted and unsubstituted, carbocyclic and heterocyclic aromatic aldehydes can be used.

Those skilled in the art of organic synthesis will appreciate that the reactivity of substituents borne by the aldehyde must be evaluated carefully, as some substituents may be transformed by the reaction conditions employed. Examples of groups that are potentially reactive under the reaction conditions are —OH, —SH, —NH$_2$ and —CO$_2$H. Suitable protecting groups or synthons for such substituents can be used, as are well known to those of skill in the art, for substituents that might otherwise be transformed during the aldol condensation or subsequent reaction steps. These "protecting" groups can be chosen, introduced and cleaved in accordance to methods described by Greene and Wuts, *Protective Groups in Organic Synthesis* 2$^{nd}$ ed., Wiley—Interscience Pub. (1991). Examples of suitable synthons are described, for example, in Hase, *Umpoled Synthons: A Survey of Sources and Uses in Synthesis*, Wiley, Europe (1987). The contents of these publications are hereby incorporated by reference in their entirety.

Variation in the Length of the Linker

The compounds of the present invention can contain more than one carbon in the linker between the heteroaromatic ring and azabicyclic ring functionalities. The manner in which such compounds as 2-(2-(3-pyridinyl)ethyl)-1-azabicyclo[2.2.2]octane, 2-(3-(3-pyridinyl)propyl)-1-azabicyclo[2.2.2]octane, and 2-(4-(3-pyridinyl)butyl)-1-azabicyclo[2.2.2]octane can be prepared can vary. For example, 2-(2-(3-pyridinyl)ethyl)-1-azabicyclo[2.2.2]octane can be prepared by different methods. In one approach, 3-pyridineacetaldehyde (also known as 2-(3-pyridinyl)ethanal) can be condensed with 3-quinuclidinone hydrochloride (commercially available from Aldrich Chemical Company) in a directed aldol reaction using a base such as potassium hydroxide or sodium hydroxide in methanol or sodium ethoxide in ethanol. Directed aldol condensations between an aldehyde and a ketone with accompanying reaction modifications, including procedures utilizing various enol ethers, are described in Smith and March, *Advanced Organic Chemistry, Reactions, Mechanisms, and Structure*, 5$^{th}$ ed., Wiley-Interscience Pubs., pp. 1220-1221 (2001). Depending on reaction conditions, condensation products may or may not spontaneously dehydrate to give enones. Thus, it may be necessary to treat the intermediate condensation products, such as 2-(1-hydroxy-2-(3-pyridinyl)ethyl)-1-azabicyclo[2.2.2]octan-3-one, under any of various dehydration protocols, known to those skilled in the art, to generate, in this case, 2-(2-(3-pyridinyl)ethylidene)-1-azabicyclo[2.2.2]octan-3-one. The carbon-carbon double bond of this unsaturated ketone can be reduced by hydrogenation to give the ketone, 2-(2-(3-pyridinyl)ethyl)-1-azabicyclo[2.2.2]octan-3-one, which can be further reduced under Wolff-Kishner conditions to yield 2-(2-(3-pyridinyl)ethyl)-1-azabicyclo[2.2.2]octane. Methods similar to those described by Yanina et al., *Khim.-Farm. Zh.* 21(7): 808 (1987) can be used for the latter reductions. Alternatively, the ketone can be reduced to the alcohol using sodium borohydride and the alcohol subsequently reduced to the alkane by conversion to the chloro intermediate (using thionyl chloride), followed by Raney nickel reduction. Replacement of 2-(3-pyridinyl)ethanal in the above synthetic approach with 3-(3-pyridinyl)propanal leads to 2-(3-(3-pyridinyl)propyl)-1-azabicyclo[2.2.2]octane and the corresponding synthetic intermediates. Replacement of 2-(3-pyridinyl)ethanal in the above synthetic approach with 4-(3-pyridinyl)butanal leads to 2-(4-(3-pyridinyl)butyl)-1-azabicyclo[2.2.2]octane and the corresponding synthetic intermediates. In all cases, the saturated ketone and alcohol intermediates provide a synthetic approach to compounds of the present invention (see section entitled "Substituted 2-(Arylalkyl)-1-azabicycloalkanes").

The requisite aldehydes for the above aldol condensations can be prepared by various methods. In one approach, 3-pyridineacetaldehyde (also known as 2-(3-pyridinyl)ethanal) can be prepared from 3-pyridinylacetic acid hydrochloride (commercially available from Aldrich Chemical Company and Lancaster Synthesis, Inc.) through the intermediacy of the ester. Thus, treatment with trimethylsilyl chloride and triethylamine generates the trimethylsilyl ester, which can then be reduced with diisobutylaluminum hydride according to the method of Chandrasekhar et al., *Tet. Lett.* 39: 909 (1998). Alternatively, 3-pyridineacetaldehyde can be prepared from 3-(3-pyridinyl)acrylic acid (commercially available from Aldrich Chemical Company and Lancaster Synthesis, Inc.) using the method of Hey et al., *J. Chem. Soc.* Part II: 1678 (1950). In this method, 3-(3-pyridinyl)acrylic acid can be converted to its acid chloride by treatment with thionyl chloride. Subsequent treatment of the acid chloride with ammonia, according to the method of Panizza, *Helv. Chim. Acta* 24: 24E (1941), yields β-(3-pyridinyl)acrylamide. Hofmann rearrangement of the latter amide by treatment with sodium hypochlorite affords methyl 2-(3-pyridinyl)vinylcarbamate, which can be hydrolyzed with refluxing 3 M sulfuric acid in ethanol to give 3-pyridineacetaldehyde, which can be isolated as its 2,4-dinitrophenylhydrazone sulfate.

The aldehyde, 3-(3-pyridinyl)propanal, which can be used to prepare 2-(3-(3-pyridinyl)propyl)-1-azabicyclo[2.2.2]octane and related compounds, can be prepared from 3-(3-pyridinyl)propanol (commercially available from Aldrich Chemical Company and Lancaster Synthesis, Inc.). Oxidation of the latter alcohol, for example, with lead acetate in pyridine, according to the method of Ratcliffe et al., *J. Chem. Soc., Perkin Trans.* 1 8: 1767 (1985), affords 3-(3-pyridinyl)propanal. Alternatively, 3-(3-pyridinyl)propanal can be prepared by Swern oxidization of 3-(3-pyridinyl)propanol using oxalyl chloride in dimethyl sulfoxide and dichloromethane according to the methods of Stocks et al., *Tet. Lett.* 36(36): 6555 (1995) and Mancuso et al., *J. Org. Chem.* 44(23): 4148 (1979).

The aldehyde, 4-(3-pyridinyl)butanal, required for the preparation of 2-(4-(3-pyridinyl)butyl)-1-azabicyclo[2.2.2]octane and related compounds can be prepared from 3-(3-pyridinyl)propanol (commercially available from Aldrich Chemical Company and Lancaster Synthesis, Inc.) by a homologative process according to the method of Solladié et al., *Tetrahedron: Asymmetry* 8(5): 801 (1997). Treatment of 3-(3-pyridinyl)propanol with tribromoimidazole and triphenylphosphine yields 1-bromo-3-(3-pyridinyl)propane, which can be condensed with the lithium salt of 1,3-dithiane. Hydrolysis of the dithianyl group of the resulting compound with aqueous mercuric chloride and mercuric oxide affords 4-(3-pyridinyl)butanal.

In yet another approach to the synthesis of 2-(2-(3-pyridinyl)ethyl)-1-azabicyclo[2.2.2]octane, 3-picoline can be converted into its lithio derivative, 3-(lithiomethyl)pyridine, as described by Fraser et al., *J. Org. Chem.* 50: 3232 (1985), and reacted with quinuclidine-2-carboxaldehyde. The resulting alcohol, 2-(1-hydroxy-2-(3-pyridinyl)ethyl)-1-azabicyclo[2.2.2]octane, can then be converted to 2-(2-(3-pyridinyl)ethyl)-1-azabicyclo[2.2.2]octane by one of the sequences previously described (i.e., dehydration, catalytic hydrogenation; conversion to the chloride, dehydrohalogenation, catalytic hydrogenation; conversion to the chloride, Raney nickel reduction). The synthesis of quinuclidine-2-carboxaldehyde is described by Ricciardi and Doukas, *Heterocycles* 24: 971 (1986).

Variation in the Azabicycle

Compounds of the present invention include those in which the azabicycle is 1-azabicyclo[2.2.1]heptane. The manner in which 2-((3-pyridinyl)methyl)-1-azabicyclo[2.2.1]heptanes can be synthesized can vary. In one approach, pyridine-3-carboxaldehyde can be reacted with 1-azabicyclo[2.2.1]heptan-3-one in an aldol condensation. The aldol condensation product, 2-((3-pyridinyl)methylene)-1-azabicyclo[2.2.1]heptan-3-one, can then be converted, using reaction sequences described previously for the 1-azabicyclo[2.2.2]octane case, into 2-((3-pyridinyl)methyl)-1-azabicyclo[2.2.1]heptane. A variety of unsubstituted or substituted, carbocyclic or heterocyclic aromatic aldehydes can be employed in this sequence. The requisite 1-azabicyclo[2.2.1]heptan-3-one can be synthesized, for example, according to the methods of Wadsworth et al., U.S. Pat. No. 5,217,975 and Street et al., *J. Med. Chem.* 33: 2690 (1990).

The present invention includes compounds in which the azabicycle is 1-azabicyclo[3.2.1]octane, such as 2-((3-pyridinyl)methyl)-1-azabicyclo[3.2.1]octane. An approach similar to that described for the 2-((3-pyridinyl)methyl)-1-azabicyclo[2.2.1]heptane case can be used to synthesize 2-((3-pyridinyl)methyl)-1-azabicyclo[3.2.1]octane. Thus, the aldol condensation of pyridine-3-carboxaldehyde and 1-azabicyclo[3.2.1]octan-3-one (see Sternbach et al. *J. Am. Chem. Soc.* 74: 2215 (1952)) will generate isomeric products, 2-((3-pyridinyl)methylene)-1-azabicyclo[3.2.1]octan-3-one and 4-((3-pyridinyl)methylene)-1-azabicyclo[3.2.1]octan-3-one. These can then be chromatographically separated and the 2-((3-pyridinyl)methylene)-1-azabicyclo[3.2.1]octan-3-one treated as described before to produce 2-((3-pyridinyl)methyl)-1-azabicyclo[3.2.1]octane. A variety of unsubstituted or substituted, carbocyclic or heterocyclic aromatic aldehydes can be employed in this sequence. The requisite 1-azabicyclo[3.2.1]octan-3-one can be synthesized, for example, according to the method of Thill and Aaron, *J. Org. Chem.* 33: 4376 (1969). In all cases, the saturated ketone and alcohol intermediates provide a synthetic approach to compounds of the present invention.

Substituted 2-(Arylalkyl)-1-azabicycloalkanes

It will be immediately recognized, by those skilled in the art, that the intermediates generated during the described syntheses of 2-(arylalkyl)-1-azabicycles present many opportunities for synthesizing substituted derivatives. For instance, conjugated enones, such as 2-((3-pyridinyl)methylene)-1-azabicyclo[2.2.2]octan-3-one, are known to undergo 1,4-addition reactions when exposed to organolithium and organomagnesium reagents in the presence of cuprous salts. Such chemistry is reviewed by Posner, *Org. React.* 19: 1 (1972) and House, *Acc. Chem. Res.* 9: 59 (1976). In some cases conjugate 1,4-addition is observed even in the absence of cuprous salts. Thus, treatment of 2-((3-pyridinyl)methylene)-1-azabicyclo[2.2.2]octan-3-one with phenylmagnesium bromide in ether at −10° C. gives 2-(1-phenyl-1-(3-pyridinyl)methyl)-1-azabicyclo[2.2.2]octane-3-one as the predominant product. This ketone can then be treated with sodium borohydride to yield the alcohol, 2-(1-phenyl-1-(3-pyridinyl)methyl)-1-azabicyclo[2.2.2]octan-3-ol. This alcohol can then be reacted with neat thionyl chloride at room temperature to give 3-chloro-2-(1-phenyl-1-(3-pyridinyl)methyl)-1-azabicyclo[2.2.2]octane as a crystalline solid. The chlorine can be removed by hydrogenation in the presence of Raney nickel, as described by de Koning, *Org. Prep. Proced. Int* 7: 31 (1975), to give 2-(1-phenyl-1-(3-pyridinyl)methyl)-1-azabicyclo[2.2.2]octane. Using variations on this approach, a number of alkyl and aryl substituents can be installed on the linker moiety between the heteroaromatic (e.g., pyridine) and azabicyclic (e.g., quinuclidine) rings.

The saturated ketone intermediates, such as 2-((3-pyridinyl)methyl)-1-azabicyclo[2.2.2]octan-3-one, also present opportunities for derivatization. One example is the reaction with phosphorus ylids (Wittig and Horner-Emmons reagents) to give alkenes. These alkenes can subsequently be reduced to alkanes by catalytic hydrogenation, providing a means of producing 2-((heteroaryl)alkyl)-1-azabicycles with alkyl and substituted alkyl substituents at the 3-position of the azabicycle. Thus, by way of example, 2-((3-pyridinyl)methyl)-1-azabicyclo[2.2.2]octan-3-one reacts with methylenetriphenylphosphorane to give 3-methylene-2-((3-pyridinyl)methyl)-1-azabicyclo[2.2.2]octane. Hydrogenation of this alkene, for example, over palladium on carbon catalyst, yields 3-methyl-2-((3-pyridinyl)methyl)-1-azabicyclo[2.2.2]octane as predominantly the cis diastereomer.

Another illustration of derivatization of saturated ketone intermediates is the reductive amination to give amines. Thus, 2-((3-pyridinyl)methyl)-1-azabicyclo[2.2.2]octan-3-one reacts with ammonium formate, zinc chloride and sodium cyanoborohydride to give 3-amino-2-((3-pyridinyl)methyl)-1-azabicyclo[2.2.2]octane as predominantly the cis diastereomer. Likewise, reaction of 2-((3-pyridinyl)methyl)-1-azabicyclo[2.2.2]octan-3-one with methylamine and sodium cyanoborohydride provides 3-(methylamino)-2-((3-pyridinyl)methyl)-1-azabicyclo[2.2.2]octane. These amine derivatives can be used as a template for library formation by reacting them with a variety of acylating agents (e.g., acid chlorides, acid anhydrides, active esters, and carboxylic acids in the presence of coupling reagents) and isocyanates to produce 2-((3-pyridinyl)methyl)-1-azabicyclo[2.2.2]octanes with amide and urea substituents in the 3-position of the 1-azabicyclo[2.2.2]octane, both of which classes are compounds of the present invention. Commercially unavailable isocyanates can be prepared in situ from corresponding amines and triphosgene in the presence of triethylamine. Such derivatives can be produced as single enantiomers, using the single enantiomers of 3-amino-2-((3-pyridinyl)methyl)-1-azabicyclo[2.2.2]octane and 3-(methylamino)-2-((3-pyridinyl)methyl)-1-azabicyclo[2.2.2]octane as starting materials. For instance, the (2R,3R)- and (2S,3S)-3-amino-2-((3-pyridinyl)methyl)-1-azabicyclo[2.2.2]octanes can be produced by resolution of the cis 3-amino-2-((3-pyridinyl)methyl)-1-azabicyclo[2.2.2]octane, for example, using diastereomeric amides. Thus, when the cis amine is reacted with a chiral acid such as (S)—N-(tert-butoxycarbonyl)proline using a suitable coupling agent such as diphenylchlorophosphate, a pair of diastereomeric amides, separable by reverse phase chromatography, is produced. The separated proline amides can then be deprotected, for example, by treatment with trifluoroacetic acid (to remove the tert-butoxycarbonyl protecting group) and then the proline can be cleaved from the desired amine, for example, using Edman degradation conditions (i.e., phenylisothiocyanate, followed by trifluoroacetic acid).

Alternatively, racemic reductive amination products such as 3-amino-2-((3-pyridinyl)methyl)-1-azabicyclo[2.2.2]octane can be separated into their enantiomers by fractional crystallization of the di-O-p-toluoyltartaric acid salts. Both the D (S,S) and L (R,R) isomers of this acid are commercially available (Aldrich Chemical Company). Thus, combination of the racemic cis 3-amino-2-((3-pyridinyl)methyl)-1-azabicyclo[2.2.2]octane with 0.5 molar equivalents of either enantiomer of di-O-p-toluoyltartaric acid yields a diastereomeric salt mixture, from which a single diastereomer precipitates from methanol solution.

The saturated alcohol intermediates, such as 2-((3-pyridinyl)methyl)-1-azabicyclo[2.2.2]octan-3-ol, can also serve as templates for compound libraries. For instance, ethers can be generated from these alcohols, for example, using either Mitsunobu or Williamson conditions. Thus, by way of example, when 2-((3-pyridinyl)methyl)-1-azabicyclo[2.2.2]octan-3-ol is reacted with phenol via Mitsunobu coupling with diethylazidocarboxylate and triphenylphosphine (Guthrie et al., *J. Chem. Soc., Perkin Trans I* 45: 2328 (1981)), 3-phenoxy-2-((3-pyridinyl)methyl)-1-azabicyclo[2.2.2]octane results. Similarly, when 2-((3-pyridinyl)methylene)-1-azabicyclo[2.2.2]octan-3-ol is treated with sodium hydride and methyl iodide, the unsaturated ether, 3-methoxy-2-((3-pyridinyl)methylene)-1-azabicyclo[2.2.2]octane, is formed. This gives the saturated ether, 3-methoxy-2-((3-pyridinyl)methyl)-1-azabicyclo[2.2.2]octane (predominantly cis), upon catalytic hydrogenation.

The saturated alcohol intermediates can also be reacted with acylating agents (e.g., acid chlorides and anhydrides) and isocyanates to produce esters and carbamates, respectively. Thus, by way of example, 2-((3-pyridinyl)methyl)-1-azabicyclo[2.2.2]octan-3-ol reacts with phenylisocyanate to yield 3-(N-phenylcarbamoyloxy)-2-((3-pyridinyl)methyl)-1-azabicyclo[2.2.2]octane. Such carbamate compounds are compounds of the present invention.

Such derivatives can be produced as single enantiomers, using the single enantiomers of 2-((3-pyridinyl)methyl)-1-azabicyclo[2.2.2]octan-3-ol as starting materials. For instance, the (2R,3R)- and (2S,3S)-2-((3-pyridinyl)methyl)-1-azabicyclo[2.2.2]octan-3-ols can be produced by resolution of the cis 2-((3-pyridinyl)methyl)-1-azabicyclo[2.2.2]octan-3-ol, using diastereomeric esters. Thus, when the cis alcohol is reacted with (S)-2-methoxy-2-phenylacetic acid and N,N-dicyclohexylcarbodiimide, a pair of diastereomeric esters, separable by reverse phase chromatography, is produced. The separated esters can then be hydrolyzed to the enantiomerically pure alcohols, for example, using potassium hydroxide in methanol. Alternatively (1S)-(−)-camphanic acid chloride can be used to produce diastereomeric camphanate esters of cis 2-((3-pyridinyl)methyl)-1-azabicyclo[2.2.2]octan-3-ol. The esters are then fractionally crystallized, using the procedure described by Swaim, et al., *J. Med. Chem.* 38: 4793 (1995).

A number of compounds possessing substituents at the 5-position of the pyridine ring can be prepared from 2-((5-bromo-3-pyridinyl)methyl)-1-azabicyclo[2.2.2]octane, the synthesis of which has already been described. For example, the 5-amino-substituted compound can be prepared from the corresponding 5-bromo compound, using ammonia in the presence of a copper catalyst according to the general method of Zwart et al., *Recueil Tray. Chim. Pays-Bas* 74: 1062 (1955). 5-Alkylamino-substituted compounds can be prepared in a similar manner. 5-Alkoxy-substituted analogs can be prepared from the corresponding 5-bromo compounds by heating with a sodium alkoxide in N,N-dimethylformamide or by use of a copper catalyst according to the general techniques described by Comins et al., *J. Org. Chem.* 55: 69 (1990) and den Hertog et al., *Recueil Trav. Chim. Pays-Bas* 74: 1171 (1955). 5-Ethynyl-substituted compounds can be prepared from the appropriate 5-bromo compounds by palladium-catalyzed coupling using 2-methyl-3-butyn-2-ol, followed by base (sodium hydride) catalyzed deprotection, according to the general techniques described by Cosford et al., *J. Med. Chem.* 39: 3235 (1996). The 5-ethynyl analogs can be converted into the corresponding 5-ethenyl, and subsequently to the corresponding 5-ethyl analogs by successive catalytic hydrogenation reactions. The 5-phenyl analogs can be prepared from the 5-bromo compounds by Suzuki coupling with phenylboronic acid. Substituted phenylboronic acids can also be used. The 5-azido-substituted analogs can be prepared from the corresponding 5-bromo compounds by reaction with sodium azide in N,N-dimethylformamide. 5-Alkylthio-substituted analogs can be prepared from the corresponding 5-bromo compound by reaction with an appropriate alkylmercaptan in the presence of sodium, using techniques known to those skilled in the art of organic synthesis.

A number of 5-substituted analogs of the aforementioned compounds can be synthesized from the corresponding 5-amino compounds via the 5-diazonium salt intermediates. Among the other 5-substituted analogs that can be produced from 5-diazonium salt intermediates are: 5-hydroxy analogs, 5-fluoro analogs, 5-chloro analogs, 5-bromo analogs, 5-iodo analogs, 5-cyano analogs, and 5-mercapto analogs. These compounds can be synthesized using the general techniques set forth in Zwart et al., *Recueil Trav. Chim. Pays-Bas* 74: 1062 (1955). For example, 5-hydroxy-substituted analogs can be prepared from the reaction of the corresponding 5-diazonium salt intermediates with water. 5-Fluoro-substituted analogs can be prepared from the reaction of the 5-diazonium salt intermediates with fluoroboric acid. 5-Chloro-substituted analogs can be prepared from the reaction of the 5-amino compounds with sodium nitrite and hydrochloric acid in the presence of copper chloride. 5-Cyano-substituted analogs can be prepared from the reaction of the corresponding 5-diazonium salt intermediates with potassium copper cyanide. 5-Amino-substituted analogs can also be converted to the corresponding 5-nitro analogs by reaction with fuming sulfuric acid and peroxide, according to the general techniques described in Morisawa, *J. Med. Chem.* 20: 129 (1977) for converting an aminopyridine to a nitropyridine. Appropriate 5-diazonium salt intermediates can also be used for the synthesis of mercapto-substituted analogs using the general techniques described in Hoffman et al., *J. Med. Chem.* 36: 953 (1993). The 5-mercapto-substituted analogs can in turn be converted to the 5-alkylthio-substituted analogs by reaction with sodium hydride and an appropriate alkyl bromide. 5-Acylamido analogs of the aforementioned compounds can be prepared by reaction of the corresponding 5-amino compounds with an appropriate acid anhydride or acid chloride, using techniques known to those skilled in the art of organic synthesis.

5-Hydroxy-substituted analogs of the aforementioned compounds can be used to prepare corresponding 5-alkanoyloxy-substituted compounds by reaction with the appropriate acid, acid chloride, or acid anhydride. Likewise, the 5-hydroxy compounds are precursors of both the 5-aryloxy and 5-heteroaryloxy analogs via nucleophilic aromatic substitution at electron deficient aromatic rings (e.g., 4-fluorobenzonitrile and 2,4-dichloropyrimidine). Such chemistry is well known to those skilled in the art of organic synthesis. Ether derivatives can also be prepared from the 5-hydroxy compounds by alkylation with alkyl halides and a suitable base or via Mitsunobu chemistry, in which a trialkyl- or triarylphosphine and diethyl azodicarboxylate are typically used. See Hughes, *Org. React.* (*N.Y.*) 42: 335 (1992) and Hughes, *Org. Prep. Proced. Int.* 28: 127 (1996) for typical Mitsunobu conditions.

5-Cyano-substituted analogs of the aforementioned compounds can be hydrolyzed to afford the corresponding 5-carboxamido-substituted compounds. Further hydrolysis results in formation of the corresponding 5-carboxylic acid-substituted analogs. Reduction of the 5-cyano-substituted analogs with lithium aluminum hydride yields the corresponding 5-aminomethyl analogs. 5-Acyl-substituted analogs can be prepared from corresponding 5-carboxylic acid-substituted analogs by reaction with an appropriate alkyllithium reagent using techniques known to those skilled in the art of organic synthesis.

5-Carboxylic acid-substituted analogs of the aforementioned compounds can be converted to the corresponding esters by reaction with an appropriate alcohol and acid catalyst. Compounds with an ester group at the 5-pyridinyl position can be reduced, for example, with sodium borohydride or lithium aluminum hydride to produce the corresponding 5-hydroxymethyl-substituted analogs. These analogs in turn can be converted to compounds bearing an alkoxymethyl moiety at the 5-pyridinyl position by reaction, for example, with sodium hydride and an appropriate alkyl halide, using conventional techniques. Alternatively, the 5-hydroxymethyl-substituted analogs can be reacted with tosyl chloride to provide the corresponding 5-tosyloxymethyl analogs. The 5-carboxylic acid-substituted analogs can also be converted to the corresponding 5-alkylaminoacyl analogs by sequential treatment with thionyl chloride and an appropriate alkylamine. Certain of these amides are known to readily undergo nucleophilic acyl substitution to produce ketones. Thus, the so-called Weinreb amides (N-methoxy-N-methylamides) react with aryllithium reagents to produce the corresponding diaryl ketones. For example, see Selnick et al., *Tet. Lett.* 34: 2043 (1993).

5-Tosyloxymethyl-substituted analogs of the aforementioned compounds can be converted to the corresponding 5-methyl-substituted compounds by reduction with lithium aluminum hydride. 5-Tosyloxymethyl-substituted analogs of the aforementioned compounds can also be used to produce 5-alkyl-substituted compounds via reaction with an alkyl lithium salt. 5-Hydroxy-substituted analogs of the aforementioned compounds can be used to prepare 5-N-alkylcarbamoyloxy-substituted compounds by reaction with N-alkylisocyanates. 5-Amino-substituted analogs of the aforementioned compounds can be used to prepare 5-N-alkoxycarboxamido-substituted compounds by reaction with alkyl chloroformate esters, using techniques known to those skilled in the art of organic synthesis.

Analogous chemistries to those described hereinbefore, for the preparation of the 5-substituted analogs of compounds of the present invention, can be employed for the synthesis of 2-, 4-, and 6-substituted analogs. Starting materials for these transformations include the aforementioned 2-((4- and 6-bromo-3-pyridinyl)methyl)-1-azabicyclo[2.2.2]octanes, as well as the 2((2-, 4-, and 6-amino-3-pyridinyl)methyl)-1-azabicyclo[2.2.2]octanes, which are accessible from 2-((3-pyridinyl)methyl)-1-azabicyclo[2.2.2]octane via the Chichibabin reaction (Lahti et al., *J. Med. Chem.* 42: 2227 (1999).

The compounds can be isolated and purified using methods well known to those of skill in the art, including, for example, crystallization, chromatography and/or extraction.

The compounds of Formulas 1 and 2 can be obtained in optically pure form by separating their racemates in accordance with the customary methods or by using optically pure starting materials.

The compounds of Formulas 1 and 2 can optionally be converted into addition salts with a mineral or organic acid by the action of such an acid in an appropriate solvent, for example, an organic solvent such as an alcohol, a ketone, an ether or a chlorinated solvent. These salts likewise form part of the invention.

Representative pharmaceutically acceptable salts include, but are not limited to, benzenesulphonate, bromide, chloride, citrate, ethanesulphonate, fumarate, gluconate, iodate, maleate, isethionate, methanesulphonate, methylenebis(β-oxynaphthoate), nitrate, oxalate, palmoate, phosphate, salicylate, succinate, sulphate, tartrate, theophyllinacetate, p-toluenesulphonate, hemigalactarate and galactarate salts.

Imaging Agents

Certain compounds of the present invention (e.g., the amide derivatives of 3-amino-2-((3-pyridinyl)methyl)-1-azabicyclo[2.2.2]octane) can be synthesized in such a manner as to incorporate a radionuclide useful in diagnostic imaging. Of particular interest are those compounds that include radioactive isotopic moieties such as $^{11}C$, $^{18}F$, $^{76}Br$, $^{123}I$, $^{125}I$, and the like. The compounds can be radiolabeled at any of a variety of positions. For example, a radionuclide of the halogen series may be used within an alkyl halide or aryl halide moiety or functionality; while a radionuclide such as $^{11}C$ may be used with an alkyl (e.g., methyl) moiety or functionality.

For instance, commercially available p-(dimethylamino) benzoic acid (Aldrich) is converted, by treatment with iodomethane in methanol, into p-(trimethylammonium)benzoate, as described by Willstaetter and Kahn, Chem. Ber. 37: 406 (1904). The displacement of the trimethylammonium group by fluoride has been reported, in similar compounds, by several researchers (see, for instance, Mach et al., J. Med. Chem. 36: 3707 (1993) and Jalalian et al., J. Labelled Compd. Radiopharm. 43: 545 (2000)). These nucleophilic aromatic substitution reactions are typically carried out in dimethylsulfoxide (with or without water cosolvent), using KF or CsF as the source of fluoride ion (when KF is used, often Kryptofix® 222 is added). When $^{18}F$ is used in such a displacement, p-$^{18}$fluorobenzoic acid results. This carboxylic acid can be rapidly coupled to 3-amino-2-((3-pyridinyl)methyl)-1-azabicyclo[2.2.2]octane, using any of a variety of techniques known to those skilled in the art (some of which are described previously), to generate N-(2-((3-pyridinyl)methyl)-1-azabicyclo[2.2.2]oct-3-yl)-4-$^{18}$fluorobenzamide, which can be used to specifically image α7 nAChRs.

Those compounds that include an amide or urea functionality (i.e., X and/or Z=NR', R'=H) can be readily radiolabeled by alkylating the amide or urea group with a radiolabeled haloalkane in the presence of a base (i.e., to form substituted compounds where R' is a radiolabeled lower alkyl, cycloalkyl or arylalkyl moiety). One example of such a radiolabeled haloalkane is $^{11}C$-labeled methyl iodide. Methods similar to those described by A. G. Horti et al., J. Med. Chem. 41: 4199-4206 (1998) can be used. The resulting N-[$^{11}C$]methyl-containing compounds can be purified by semi-preparative or preparative HPLC and briefly isolated for reconstitution. The $^{11}C$-labeled methyl iodide can be prepared according to the general method described by B. Långström et al. J. Nucl. Med. 28(6):1037-1040 (1987). Thus, nitrogen gas is irradiated with 10 MeV protons producing $^{11}C$-carbon dioxide. The $^{11}C$-carbon dioxide is trapped using 4 Å molecular sieves, which are subsequently stored in a lead shield. The $^{11}C$-carbon dioxide is liberated from the 4 Å molecular sieves by heating to −250° C. The $^{11}C$-carbon dioxide is then carried in a stream of nitrogen and trapped in a vessel containing lithium aluminum hydride in tetrahydrofuran. The tetrahydrofuran is removed by heating and a nitrogen flow, and the lithium aluminum hydride complex is then hydrolyzed by treatment with hydriodic acid, affording $^{11}C$-labeled methyl iodide. The $^{11}C$-labeled methyl iodide can be transferred by carrier gas to the reaction vessel containing the material to be methylated. The required amide- and urea-containing precursor compounds are described in detail above, and the resulting radiolabeled compounds can also be used to specifically image α7 nAChRs.

II. Pharmaceutical Compositions

The compounds described herein can be incorporated into pharmaceutical compositions and used to prevent a condition or disorder in a subject susceptible to such a condition or disorder, and/or to treat a subject suffering from the condition or disorder. The pharmaceutical compositions described herein include one or more compounds of Formulas 1 and 2 and/or pharmaceutically acceptable salts thereof. Chiral compounds can be employed as racemic mixtures or as pure enantiomers.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions can be formulated in unit dose form, or in multiple or subunit doses. Preferred compositions are in liquid or semisolid form. Compositions including a liquid pharmaceutically inert carrier such as water or other pharmaceutically compatible liquids or semisolids can be used. The use of such liquids and semisolids is well known to those of skill in the art.

The compositions can also be administered via injection, i.e., intravenously, intramuscularly, subcutaneously, intraperitoneally, intraarterially, intrathecally; and intracerebroventricularly. Intravenous administration is the preferred method of injection. Suitable carriers for injection are well known to those of skill in the art and include 5% dextrose solutions, saline, and phosphate-buffered saline. The compounds can also be administered as an infusion or injection (e.g., as a suspension or as an emulsion in a pharmaceutically acceptable liquid or mixture of liquids).

The formulations can also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations can depend on the particular composition used and the particular subject receiving the treatment. These formulations can contain a liquid carrier that can be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, upon administration, the active ingredients interact with receptor sites within the body of the subject that affect the functioning of the CNS. More specifically, in treating a CNS disorder, preferable administration is designed to optimize the effect upon those relevant nicotinic acethylcholine receptor (nAChR) subtypes that have an effect upon the functioning of the CNS, while minimizing the effects upon muscle-type receptor subtypes. Other suitable methods for administering the compounds of the present invention are described in U.S. Pat. No. 5,604,231 to Smith et al., the contents of which are hereby incorporated by reference.

In certain circumstances, the compounds described herein can be employed as part of a pharmaceutical composition with other compounds intended to prevent or treat a particular disorder. In addition to effective amounts of the compounds described herein, the pharmaceutical compositions can also include various other components as additives or adjuncts. Exemplary pharmaceutically acceptable components or adjuncts which are employed in relevant circumstances include antioxidants, free-radical scavenging agents, peptides, growth factors, antibiotics, bacteriostatic agents, immunosuppressives, anticoagulants, buffering agents, anti-inflammatory agents, anti-pyretics, time-release binders, anesthetics, steroids, vitamins, minerals and corticosteroids. Such components can provide additional therapeutic benefit, act to affect the therapeutic action of the pharmaceutical composition, or act towards preventing any potential side effects that can be imposed as a result of administration of the pharmaceutical composition.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating a CNS disorder, an effective amount of compound is an amount sufficient to pass across the blood-brain barrier of the subject, to bind to relevant receptor sites in the brain of the subject and to modulate the activity of relevant nAChR subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the recurrence of the symptoms of the disorder. Preferably, the effective amount is sufficient to obtain the desired result, but insufficient to cause appreciable side effects.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to modulate the activity of relevant nAChRs to effect neurotransmitter (e.g., dopamine) release, but the amount should be insufficient to induce effects on skeletal muscles and ganglia to any significant degree. The effective dose of compounds will of course differ from patient to patient, but in general includes amounts starting where CNS effects or other desired therapeutic effects occur but below the amount where muscular effects are observed.

The compounds, when employed in effective amounts in accordance with the method described herein, are selective to certain relevant nAChRs, but do not significantly activate receptors associated with undesirable side effects at concentrations at least greater than those required for eliciting the release of dopamine or other neurotransmitters. By this is meant that a particular dose of compound effective in preventing and/or treating a CNS disorder is essentially ineffective in eliciting activation of certain ganglionic-type nAChRs at concentration higher than 5 times, preferably higher than 100 times, and more preferably higher than 1,000 times than those required for modulation of neurotransmitter release. This selectivity of certain compounds described herein against those ganglionic-type receptors responsible for cardiovascular side effects is demonstrated by a lack of the ability of those compounds to activate nicotinic function of adrenal chromaffin tissue at concentrations greater than those required for activation of dopamine release.

The compounds described herein, when employed in effective amounts in accordance with the methods described herein, can provide some degree of prevention of the progression of CNS disorders, ameliorate symptoms of CNS disorders, and ameliorate to some degree of the recurrence of CNS disorders. The effective amounts of those compounds are typically below the threshold concentration required to elicit any appreciable side effects, for example those effects relating to skeletal muscle. The compounds can be administered in a therapeutic window in which certain CNS disorders are treated and certain side effects are avoided. Ideally, the effective dose of the compounds described herein is sufficient to provide the desired effects upon the CNS but is insufficient (i.e., is not at a high enough level) to provide undesirable side effects. Preferably, the compounds are administered at a dosage effective for treating the CNS disorders but less than ⅕, and often less than ¹⁄₁₀, the amount required to elicit certain side effects to any significant degree.

Most preferably, effective doses are at very low concentrations, where maximal effects are observed to occur, with a minimum of side effects. Typically, the effective dose of such compounds generally requires administering the compound in an amount of less than 5 mg/kg of patient weight. Often, the compounds of the present invention are administered in an amount from less than about 1 mg/kg patent weight and usually less than about 100 µg/kg of patient weight, but frequently between about 10 µg to less than 100 µg/kg of patient weight. For compounds that do not induce effects on muscle-type nicotinic receptors at low concentrations, the effective dose is less than 5 mg/kg of patient weight; and often such compounds are administered in an amount from 50 µg to less than 5 mg/kg of patient weight. The foregoing effective doses typically represent that amount administered as a single dose, or as one or more doses administered over a 24-hour period.

For human patients, the effective dose of typical compounds generally requires administering the compound in an amount of at least about 1, often at least about 10, and frequently at least about 100 mg/24 hr/patient. For human patients, the effective dose of typical compounds requires administering the compound which generally does not exceed about 500, often does not exceed about 400, and frequently does not exceed about 300 mg/24 hr/patient. In addition, the compositions are advantageously administered at an effective dose such that the concentration of the compound within the plasma of the patient normally does not exceed 50 ng/mL, often does not exceed 30 ng/mL, and frequently does not exceed 10 ng/mL.

III. Methods of Using the Compounds and/or Pharmaceutical Compositions

The compounds can be used to treat those types of conditions and disorders for which other types of nicotinic compounds have been proposed as therapeutics. See, for example, Williams et al., *Drug News Perspec.* 7(4):205 (1994), Arneric et al., *CNS Drug Rev.* 1(1):1 (1995), Arneric et al., *Exp. Opin. Invest. Drugs* 5(1):79 (1996), Bencherif et al., *J. Pharmacol. Exp. Ther.* 279:1413 (1996), Lippiello et al., *J. Pharmacol. Exp. Ther.* 279:1422 (1996), Damaj et al., *J. Pharmacol. Exp. Ther.* 291:390 (1999); Chiari et al., *Anesthesiology* 91:1447 (1999); Lavand'homme and Eisenbach, *Anesthesiology* 91:1455 (1999); *Neuroscience* (1997), Holladay et al., *J. Med. Chem.* 40(28):4169 (1997), Bannon et al., *Science* 279: 77 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al., the disclosures of each of which are incorporated herein by reference in their entirety.

More particularly, the compounds can be used to treat those types of conditions and disorders for which nicotinic compounds with selectivity for the α7 nAChR subtype have been proposed as therapeutics. See, for example, Leonard et al., *Schizophrenia Bulletin* 22(3): 431 (1996), Freedman et al., *Biological Psychiatry* 38(1):22 (1995), Heeschen et al., *J. Clin. Invest.* 100: 527 (2002), Utsugisawa et al., *Molecular Brain Research* 106(1-2): 88 (2002), U.S. Patent Application 2002/0016371, Levin and Rezvani, *Current Drug Targets: CNS and Neurological Disorders* 1(4): 423 (2002)), O'Neill et al., *Current Drug Targets: CNS and Neurological Disorders* 1(4): 399 (2002, Jeyarasasingam et al., *Neuroscience* 109(2): 275 (2002)), Xiao et al., *Proc. Nat. Acad. Sci. (US)* 99(12): 8360 (2002)), PCT WO 99/62505, PCT WO 99/03859, PCT WO 97/30998, PCT WO 01/36417, PCT WO 02/15662, PCT WO 02/16355, PCT WO 02/16356, PCT WO 02/16357, PCT WO 02/16358, PCT WO 02/17358, Stevens et al., *Psychopharm.* 136: 320 (1998), Dolle et al., *J. Labelled Comp. Radiopharm.* 44: 785 (2001) and Macor et al., *Bioorg. Med. Chem. Lett.* 11: 319 (2001) and references therein, the contents of each of which are hereby incorporated by reference in their entirety.

The compounds can also be used as adjunct therapy in combination with existing therapies in the management of the aforementioned types of diseases and disorders. In such situations, it is preferably to administer the active ingredients in a manner that minimizes effects upon nAChR subtypes such as those that are associated with muscle and ganglia. This can be accomplished by targeted drug delivery and/or by adjusting the dosage such that a desired effect is obtained without meeting the threshold dosage required to achieve significant side effects. The pharmaceutical compositions can be used to ameliorate any of the symptoms associated with those conditions, diseases and disorders. Representative classes of disorders that can be treated are discussed in detail below.

Treatment of CNS Disorders

Examples of conditions and disorders that can be treated include neurological disorders and neurodegenerative disorders, and, in particular, CNS disorders. CNS disorders can be drug induced; can be attributed to genetic predisposition, infection or trauma; or can be of unknown etiology. CNS disorders comprise neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine and/or serotonin.

Examples of CNS disorders that can be treated in accordance with the present invention include pre-senile dementia (early onset Alzheimer's disease), senile dementia (dementia of the Alzheimer's type), Lewy Body dementia, micro-infarct dementia, AIDS-related dementia, HIV-dementia, multiple cerebral infarcts, Parkinsonism including Parkinson's disease, Pick's disease, progressive supranuclear palsy, Huntington's chorea, tardive dyskinesia, hyperkinesia, mania, attention deficit disorder, anxiety, depression, dyslexia, schizophrenia depression, obsessive-compulsive disorders, Tourette's syndrome, mild cognitive impairment (MCI), age-associated memory impairment (AAMI), premature amnesic and cognitive disorders which are age-related or a consequence of alcoholism, or immunodeficiency syndrome, or are associated with vascular disorders, with genetic alterations (such as, for example, trisomy 21) or with attention deficiencies or learning deficiencies, acute or chronic neurodegenerative conditions such as amyotrophic lateral sclerosis, multiple sclerosis, peripheral neurotrophies, and cerebral or spinal traumas. In addition, the compounds can be used to treat nicotine addiction and/or other behavioral disorders related to substances that lead to dependency (e.g., alcohol, cocaine, heroin and opiates, psychostimulants, benzodiazepines and barbiturates).

Schizophrenia is an example of a CNS disorder that is particularly amenable to treatment by modulating the α7 nAChR subtype. The compounds can also be administered to improve cognition and/or provide neuroprotection, and these uses are also particularly amenable to treatment with compounds, such as the compounds of the present invention, that are specific for the α7 nAChR subtype.

The disorders can be treated and/or prevented by administering to a patient in need of treatment or prevention thereof an effective treatment or preventative amount of a compound that provides some degree of prevention of the progression of a CNS disorder (i.e., provides protective effects), ameliorating the symptoms of the disorder, and ameliorating the recurrence of the disorder.

Anti-Inflammatory Uses

Excessive inflammation and tumor necrosis factor synthesis cause morbidity and even mortality in a variety of diseases. These diseases include, but are not limited to, endotoxemia, sepsis, rheumatoid arthritis, and irritable bowel disease. The nervous system, primarily through the vagus nerve, is known to regulate the magnitude of the innate immune response by inhibiting the release of macrophage tumor necrosis factor (TNF). This physiological mechanism is known as the "cholinergic anti-inflammatory pathway" (see, for example, Tracey, "The inflammatory reflex," *Nature.* 420:853-9(2002)).

The nicotinic acetylcholine receptor α7 subunit is required for acetylcholine inhibition of macrophage TNF release, and also inhibits release of other cytokines. Agonists (or, at elevated dosages, partial agonists) at the α7-specific receptor subtype can inhibit the TNF-modulated inflammatory response. Accordingly, those compounds described herein that are α7 agonists can be used to treat inflammatory disorders characterized by excessive synthesis of TNF (See also Wang et al., "Nicotinic acetylcholine receptor α7 subunit is an essential regulator of inflammation", Nature, 421:384-8 (2003)).

Inflammatory conditions that can be treated or prevented by administering the compounds described herein include, but are not limited to, chronic and acute inflammation, psoriasis, gout, acute pseudogout, acute gouty arthritis, arthritis, rheumatoid arthritis, osteoarthritis, allograft rejection, chronic transplant rejection, asthma, atherosclerosis, mononuclear-phagocyte dependent lung injury, idiopathic pulmonary fibrosis, atopic dermatitis, chronic obstructive pulmonary disease, adult respiratory distress syndrome, acute chest syndrome in sickle cell disease, inflammatory bowel disease, Crohn's disease, ulcerative colitis, acute cholangitis, aphteous stomatitis, glomerulonephritis, lupus nephritis, thrombosis, and graft vs. host reaction.

Minimizing the Inflammatory Response Associated with Bacterial and/or Viral Infection Many bacterial and/or viral infections are associated with side effects brought on by the formation of toxins, and the body's natural response to the bacteria or virus and/or the toxins. Examples of such bacterial infections include anthrax, botulism, and sepsis. As discussed above, the body's response to infection often involves generating a significant amount of TNF and/or other cytokines. The over-expression of these cytokines can result in significant injury, such as septic shock (when the bacteria is sepsis), endotoxic shock, urosepsis and toxic shock syndrome.

Cytokine expression is mediated by the α7 nAChR, and can be inhibited by administering agonists or partial agonists of these receptors. Those compounds described herein that are agonists or partial agonists of these receptors can therefore be used to minimize the inflammatory response associated with bacterial infection, as well as viral and fungal infections. Certain of the compounds themselves may also have antimicrobial properties.

These compounds can also be used as adjunct therapy in combination with existing therapies to manage bacterial, viral and fungal infections, such as antibiotics, antivirals and antifungals. Antitoxins can also be used to bind to toxins produced by the infectious agents and allow the bound toxins to pass through the body without generating an inflammatory response. Examples of antitoxins are disclosed, for example, in U.S. Pat. No. 6,310,043 to Bundle et al., incorporated herein by reference. Other agents effective against bacterial and other toxins can be effective and their therapeutic effect can be complimented by co-administration with the compounds described herein.

Analgesic Uses

The compounds can be administered to treat and/or prevent pain, including neurologic, neuropathic and chronic pain. The analgesic activity of compounds described herein can be demonstrated in models of persistent inflammatory pain and of neuropathic pain, performed as described in U.S. Published Patent Application No. 20010056084 A1 (Allgeier et al.) (e.g., mechanical hyperalgesia in the complete Freund's adjuvant rat model of inflammatory pain and mechanical hyperalgesia in the mouse partial sciatic nerve ligation model of neuropathic pain).

The analgesic effect is suitable for treating pain of various genesis or etiology, in particular in treating inflammatory pain and associated hyperalgesia, neuropathic pain and associated hyperalgesia, chronic pain (e.g., severe chronic pain, postoperative pain and pain associated with various conditions including cancer, angina, renal or billiary colic, menstruation, migraine and gout). Inflammatory pain may be of diverse genesis, including arthritis and rheumatoid disease, tenosynovitis and vasculitis. Neuropathic pain includes trigeminal or herpetic neuralgia, diabetic neuropathy pain, causalgia, low back pain and deafferentation syndromes such as brachial plexus avulsion.

Inhibition of Neovascularization

The α7 nAChR is also associated with neovascularization. Inhibition of neovascularization, for example, by administering antagonists (or at certain dosages, partial agonists) of the α7 nAChR can treat or prevent conditions characterized by undesirable neovascularization or angiogenesis. Such conditions can include those characterized by inflammatory angiogenesis and/or ischemia-induced angiogenesis. Neovascularization associated with tumor growth can also be inhibited by administering those compounds described herein that function as antagonists or partial agonists of α7 nAChR.

Specific antagonism of α7 nAChR-specific activity reduces the angiogenic response to inflammation, ischemia, and neoplasia. Guidance regarding appropriate animal model systems for evaluating the compounds described herein can be found, for example, in Heeschen, C. et al., "A novel angiogenic pathway mediated by non-neuronal nicotinic acetylcholine receptors," J. Clin. Invest. 110(4):527-36 (2002), incorporated herein by reference regarding disclosure of α7-specific inhibition of angiogenesis and cellular (in vitro) and animal modeling of angiogenic activity relevant to human disease, especially the Lewis lung tumor model (in vivo, in mice—see, in particular, pages 529, and 532-533).

Representative tumor types that can be treated using the compounds described herein include NSCLC, ovarian cancer, pancreatic cancer, breast carcinoma, colon carcinoma, rectum carcinoma, lung carcinoma, oropharynx carcinoma, hypopharynx carcinoma, esophagus carcinoma, stomach carcinoma, pancreas carcinoma, liver carcinoma, gallbladder carcinoma, bile duct carcinoma, small intestine carcinoma, urinary tract carcinoma, kidney carcinoma, bladder carcinoma, urothelium carcinoma, female genital tract carcinoma, cervix carcinoma, uterus carcinoma, ovarian carcinoma, choriocarcinoma, gestational trophoblastic disease, male genital tract carcinoma, prostate carcinoma, seminal vesicles carcinoma, testes carcinoma, germ cell tumors, endocrine gland carcinoma, thyroid carcinoma, adrenal carcinoma, pituitary gland carcinoma, skin carcinoma, hemangiomas, melanomas, sarcomas, bone and soft tissue sarcoma, Kaposi's sarcoma, tumors of the brain, tumors of the nerves, tumors of the eyes, tumors of the meninges, astrocytomas, gliomas, glioblastomas, retinoblastomas, neuromas, neuroblastomas, Schwannomas, meningiomas, solid tumors arising from hematopoietic malignancies (such as leukemias, chloromas, plasmacytomas and the plaques and tumors of mycosis fungoides and cutaneous T-cell lymphoma/leukemia), and solid tumors arising from lymphomas.

The compounds can also be administered in conjunction with other forms of anti-cancer treatment, including co-administration with antineoplastic antitumor agents such as cisplatin, adriamycin, daunomycin, and the like, and/or anti-VEGF (vascular endothelial growth factor) agents, as such are known in the art.

The compounds can be administered in such a manner that they are targeted to the tumor site. For example, the compounds can be administered in microspheres, microparticles or liposomes conjugated to various antibodies that direct the microparticles to the tumor. Additionally, the compounds can be present in microspheres, microparticles or liposomes that are appropriately sized to pass through the arteries and veins, but lodge in capillary beds surrounding tumors and administer the compounds locally to the tumor. Such drug delivery devices are known in the art.

Other Disorders

In addition to treating CNS disorders, inflammatory disorders, and neovascular disorders, and inhibiting the pain response, the compounds can be also used to prevent or treat certain other conditions, diseases, and disorders. Examples include autoimmune disorders such as Lupus, disorders associated with cytokine release, cachexia secondary to infection (e.g., as occurs in AIDS, AIDS related complex and neoplasia), as well as those indications set forth in PCT WO 98/25619. The compounds can also be administered to treat convulsions such as those that are symptomatic of epilepsy, and to treat conditions such as syphillis and Creutzfeld-Jakob disease.

Diagnostic Uses

The compounds can be used in diagnostic compositions, such as probes, particularly when they are modified to include appropriate labels. The probes can be used, for example, to determine the relative number and/or function of specific receptors, particularly the α7 receptor subtype. The compounds of the present invention most preferably are labeled with a radioactive isotopic moiety such as $^{11}$C, $^{18}$F, $^{76}$Br, $^{123}$I or $^{125}$I, as discussed above.

The administered compounds can be detected using known detection methods appropriate for the label used. Examples of detection methods include position emission topography (PET) and single-photon emission computed, tomography (SPECT). The radiolabels described above are useful in PET (e.g., $^{11}$C, $^{18}$F or $^{76}$Br) and SPECT (e.g., $^{123}$I) imaging, with half-lives of about 20.4 minutes for $^{11}$C, about 109 minutes for $^{18}$F, about 13 hours for $^{123}$I, and about 16 hours for $^{76}$Br. A high specific activity is desired to visualize the selected receptor subtypes at non-saturating concentrations. The administered doses typically are below the toxic range and provide high contrast images. The compounds are expected to be capable of administration in non-toxic levels. Determination of dose is carried out in a manner known to one skilled in the art of radiolabel imaging. See, for example, U.S. Pat. No. 5,969,144 to London et al.

The compounds can be administered using known techniques. See, for example, U.S. Pat. No. 5,969,144 to London et al. The compounds can be administered in formulation compositions that incorporate other ingredients, such as those types of ingredients that are useful in formulating a diagnostic composition. Compounds useful in accordance with carrying out the present invention most preferably are employed in forms of high purity. See, U.S. Pat. No. 5,853,696 to Elmalch et al.

After the compounds are administered to a subject (e.g., a human subject), the presence of that compound within the subject can be imaged and quantified by appropriate techniques in order to indicate the presence, quantity, and functionality of selected nicotinic cholinergic receptor subtypes. In addition to humans, the compounds can also be administered to animals, such as mice, rats, dogs, and monkeys. SPECT and PET imaging can be carried out using any appropriate technique and apparatus. See Villemagne et al., In: Arneric et al. (Eds.) *Neuronal Nicotinic Receptors: Pharmacology and Therapeutic Opportunities,* 235-250 (1998) and U.S. Pat. No. 5,853,696 to Elmalch et al. for a disclosure of representative imaging techniques.

The radiolabeled compounds bind with high affinity to selective nAChR subtypes (e.g., α7) and preferably exhibit negligible non-specific binding to other nicotinic cholinergic receptor subtypes (e.g., those receptor subtypes associated with muscle and ganglia). As such, the compounds can be used as agents for noninvasive imaging of nicotinic cholinergic receptor subtypes within the body of a subject, particularly within the brain for diagnosis associated with a variety of CNS diseases and disorders.

In one aspect, the diagnostic compositions can be used in a method to diagnose disease in a subject, such as a human patient. The method involves administering to that patient a detectably labelled compound as described herein, and detecting the binding of that compound to selected nicotinic receptor subtypes (e.g., α7 receptor subtype). Those skilled in the art of using diagnostic tools, such as PET and SPECT, can use the radiolabeled compounds described herein to diagnose a wide variety of conditions and disorders, including conditions and disorders associated with dysfunction of the central and autonomic nervous systems. Such disorders include a wide variety of CNS diseases and disorders, including Alzheimer's disease, Parkinson's disease, and schizophrenia. These and other representative diseases and disorders that can be evaluated include those that are set forth in U.S. Pat. No. 5,952,339 to Bencherif et al., the contents of which are hereby incorporated by reference.

In another aspect, the diagnostic compositions can be used in a method to monitor selective nicotinic receptor subtypes of a subject, such as a human patient. The method involves administering a detectably labeled compound as described herein to that patient and detecting the binding of that compound to selected nicotinic receptor subtypes (e.g., the α7 receptor subtype).

The following examples are provided to further illustrate the present invention, and should not be construed as limiting thereof.

IV. Synthetic Examples

The following synthetic examples are provided to illustrate the present invention and should not be construed as limiting the scope thereof. In these examples, all parts and percentages are by weight, unless otherwise noted. Reaction yields are reported in mole percentage.

The first step in synthesizing the compounds of interest is to synthesize 2-((3-pyridinyl)methyl)-1-azabicyclo[2.2.2]octan-3-one, as described below:

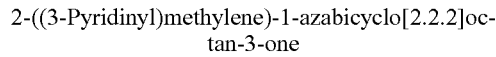

2-((3-Pyridinyl)methylene)-1-azabicyclo[2.2.2]octan-3-one

Potassium hydroxide (56 g, 0.54 mole) was dissolved in methanol (420 mL). 3-Quinuclidinone hydrochloride (75 g, 0.49 mole) was added and the mixture was stirred for 30 min at ambient temperature. 3-Pyridinecarboxaldehyde (58 g, 0.54 mole) was added and the mixture stirred for 16 h at ambient temperature. The reaction mixture became yellow during this period, with solids caking on the walls of the flask. The solids were scraped from the walls and the chunks broken up. With rapid stirring, water (390 mL) was added. When the solids dissolved, the mixture was cooled at 4° C. overnight. The crystals were collected by filtration, washed with water, and air dried to obtain 80 g of yellow solid. A second crop (8 g) was obtained by concentration of the filtrate to ~10% of its former volume and cooling at 4° C. overnight. Both crops were sufficiently pure for further transformation (88 g, 82%).

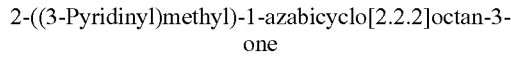

2-((3-Pyridinyl)methyl)-1-azabicyclo[2.2.2]octan-3-one 2-((3-Pyridinyl)methylene)-1-azabicyclo[2.2.2]octan-3-one (20 g, 93 mmol) was suspended in methanol (200 mL)

and treated with 46 mL of 6N HCl. 10% Palladium on carbon (1.6 g) was added and the mixture was shaken under 25 psi hydrogen for 16 h. The mixture was filtered through Celite and solvent removed from the filtrate by rotary evaporation, to give crude 2-((3-pyridinyl)methyl)-1-azabicyclo[2.2.2]octan-3-one hydrochloride as a white gum (20 g). This was treated with 2N NaOH (50 mL) and chloroform (50 mL) and stirred for an hour. The chloroform layer was separated and the aqueous phase was treated with 2N NaOH, enough to raise the pH to 10 (about 5 mL), and saturated aqueous NaCl (25 mL). This was extracted with chloroform (3×10 mL), and the combined extracts were dried ($MgSO_4$) and concentrated by rotary evaporation. The residue (18 g) was dissolved in warm ether (320 mL) and cooled to 4° C. The white solid was filtered off, washed with a small portion of cold ether and air dried. Concentration of the filtrate to ~10% of its former volume and cooling at 4° C. produced a second crop. A combined yield 16 g (79%) was obtained.

The 2-((3-pyridinyl)methyl)-1-azabicyclo[2.2.2]octan-3-one can then be used to produce the scaffolds from which the remaining examples were synthesized. The synthesis of the three scaffolds and their separation into individual enantiomers was accomplished by the following procedures.

Scaffold 1

2-((3-Pyridinyl)methyl)-1-azabicyclo[2.2.2]octan-3-ol

In accordance with the procedure reported by Warawa et al., *J. Med. Chem.* 17(5): 497 (1974), a 250 mL three-neck round bottom flask was fitted with a Vigreux column and distilling head. 2-((3-Pyridinyl)methyl)-1-azabicyclo[2.2.2]octan-3-one (3.00 g, 13.9 mmol), isopropanol (165 mL), aluminum isopropoxide (10.4 g, 50.9 mmol) and four boiling chips were added to the flask. The mixture was slowly distilled under nitrogen, the distillate being collected over a 3 h period. When the distillate no longer showed the presence of acetone (by 2,4-dinitrophenylhydrazone formation), the distillation was stopped and the reaction mixture cooled to ambient temperature. The volatiles were removed by rotary evaporation and the gelatinous residue was diluted with saturated aqueous NaCl (50 mL) and 50% aqueous NaOH (10 mL). The mixture was then extracted with chloroform (3×25 mL), and the extracts were combined, dried over $MgSO_4$, and concentrated by rotary evaporation. The resulting amber oil became a cream-colored solid (3.02 g, 99.7% yield) upon high vacuum treatment. GCMS analysis indicated that the product is a 93:7 mixture of diastereomers. That the cis relative configuration of 2-[(pyridin-3-yl)methyl]quinuclidin-3-ol was the major diastereomer was established by comparison of the 3-H chemical shift with corresponding chemical shifts of cis- and trans-2-(arylmethyl)quinuclidin-3-ols (Warawa and Campbell, *J. Org. Chem.* 39(24): 3511 (1974)).

(R,R) and (S,S)-2-((3-pyridinyl)methyl)-1-azabicyclo[2.2.2]octan-3-ol

A mixture of (cis)-2-((3-pyridinyl)methyl)-1-azabicyclo[2.2.2]octan-3-ol (1.97 g, 9.04 mmol), N,N-dicyclohexylcarbodiimide (3.73 g, 18.1 mmol), 4-dimethylaminopyridine (55 mg, 0.40 mmol), (S)-2-methoxy-2-phenylacetic acid (3.00 g, 18.1 mmol), and anhydrous dichloromethane (125 mL) was stirred at ambient temperature under nitrogen for 24 h. The precipitated N,N-dicyclohexylurea was filtered from the reaction mixture and the filtrate was extracted sequentially with water (200 mL), saturated aqueous $NaHCO_3$ (200 mL) and saturated aqueous NaCl (200 mL). The organic layer was dried ($MgSO_4$), filtered and concentrated to give a dark orange oil (4.45 g). A portion (4.2 g) of this diastereomeric mixture was dissolved in acetonitrile (8.4 mL) and separated, in portions, by preparative HPLC, using 90:10:0.1 acetonitrile/water/trifluoroacetic acid as eluent. The diastereomers exhibited retention times of 3.8 min and 4.5 min. The corresponding fractions from the various injections were combined and concentrated to yield 1.1 g (56% yield) and 0.70 g (36% yield), respectively, as clear, colorless oils. LCMS analysis of the solvent-free esters confirmed the efficiency of their separation, showing diastereomeric purities of 92% (for the 3.8 min fraction) and 95% (for the 4.5 min fraction).

In separate flasks, portions (0.175 g, 0.477 mmol) of each of the diastereomers were dissolved in methanol (2.5 mL) and treated with solutions of KOH (0.20 g, 3.6 mmol) in methanol (3 mL). These mixtures were stirred overnight at ambient temperature. The methanol was removed by evaporation, and the residues were diluted with a mixture of saturated aqueous NaCl (2 mL) and 50% NaOH (1 mL) and then extracted with chloroform (3×5 mL). For each of the hydrolyses, the organic layers were combined, dried ($MgSO_4$), filtered, and concentrated. This gave 0.061 g (59% yield) of the enantiomer derived from the 3.8 min peak and 0.056 g (54% yield) of the enantiomer derived from the 4.5 min peak. Both were clear, colorless oils.

Scaffold 2

3-Amino-2-((3-pyridinyl)methyl)-1-azabicyclo[2.2.2]octane

To a stirred solution of 2-((3-pyridinyl)methyl)-1-azabicyclo[2.2.2]octan-3-one (3.00 g, 13.9 mmol) in dry methanol (20 mL), under nitrogen, was added a 1 M solution of $ZnCl_2$ in ether (2.78 mL, 2.78 mmol). After stirring at ambient temperature for 30 min, this mixture was treated with solid ammonium formate (10.4 g, 167 mmol). After stirring another hour at ambient temperature, solid sodium cyanoborohydride (1.75 g, 27.8 mmol) was added in portions. The reaction was then stirred at ambient temperature overnight and terminated by addition of water (~5 mL). The quenched reaction was partitioned between 5 M NaOH (10 mL) and chloroform (20 mL). The aqueous layer was extracted with chloroform (20 mL), and combined organic layers were dried ($Na_2SO_4$), filtered and concentrated. This left 2.97 g of yellow gum. GC/MS analysis indicated that the product was a 90:10 mixture of the cis and trans amines, along with a trace of the corresponding alcohol (98% mass recovery).

(R,R) and (S,S)-3-amino-2-((3-pyridinyl)methyl)-1-azabicyclo[2.2.2]octane

Di-p-toluoyl-D-tartaric acid (5.33 g, 13.8 mmol) was added to a stirred solution of crude 3-amino-2-((3-pyridinyl)methyl)-1-azabicyclo[2.2.2]octane (6.00 g, 27.6 mmol of 9:1 cis/trans) in methanol (20 mL). After complete dissolution, the clear solution was then concentrated to a solid mass by rotary evaporation. The solid was dissolved in a minimum amount of boiling methanol (~5 mL). The solution was cooled slowly, first to ambient temperature (1 h), then for ~4 h at 5° C. and finally at −5° C. overnight. The precipitated salt was collected by suction filtration and recrystallized from 5 mL of methanol. Drying left 1.4 g of white solid, which was partitioned between chloroform (5 mL) and 2 M NaOH (5 mL). The chloroform layer and a 5 mL chloroform extract of the aqueous layer were combined, dried (Na$_2$SO$_4$) and concentrated to give a colorless oil (0.434 g). The enantiomeric purity of this free base was determined by conversion of a portion into its N-(tert-butoxycarbonyl)-L-prolinamide, which was then analyzed for diastereomeric purity (98%) using LCMS.

The mother liquor from the initial crystallization was made basic (~pH 11) with 2 M NaOH and extracted twice with chloroform (10 mL). The chloroform extracts were dried (Na$_2$SO$_4$) and concentrated to give an oil. This amine (3.00 g, 13.8 mmol) was dissolved in methanol (10 mL) and treated with di-p-toluoyl-L-tartaric acid (2.76 g, 6.90 mmol). The mixture was warmed to aid dissolution and then cooled slowly to −5° C., where it remained overnight. The precipitate was collected by suction filtration, recrystallized and dried. This left 1.05 g of white solid. The salt was converted into the free base as described above for the other isomer (yield=0.364 g), and the enantiomeric purity (97%) was assessed using the prolinaminde method, described above.

Scaffold 3

3-Aminomethyl-2-((3-pyridinyl)methyl)-1-azabicyclo[2.2.2]octane 2-((3-Pyridinyl)methyl)-1-azabicyclo[2.2.2]octan-3-one (2.16 g, 0.01 mol), methylamine (25 mL, 0.05 mol) and zinc chloride (5 mL, 0.005 mol) were added to dry methanol (30 mL) and stirred at room temperature for 30 min. Then, sodium cyanoborohydride (30 mL, 1.0M in THF) was added carefully and the mixture stirred at room temperature for 48 h. The mixture was adjusted to pH 10 using 2N potassium hydroxide and then the solvent was removed by rotary evaporation. The residue was extracted with chloroform (3×50 mL), dried (MgSO$_4$), filtered and concentrated by rotary evaporation to yield the crude desired amine as a light yellow oil (2.40 g, 83% yield). The product was taken on to the next step without further purification.

The following example describes the synthesis of various 2-((3-pyridinyl)methyl)-1-azabicyclo[2.2.2]oct-3-yl N-arylcarbamates, which are built upon Scaffold 1. Table 1 shows a list of various compounds within this example that were synthesized.

Example 1

2-((3-Pyridinyl)methyl)-1-azabicyclo[2.2.2]oct-3-yl N-arylcarbamates

Various aryl isocyanates (0.2 mmol) were combined with 2-((3-pyridinyl)methyl)-1-azabicyclo[2.2.2]octan-3-ol (0.2 mmol) in anhydrous toluene (1 mL). The reaction mixtures were heated at 100° C. for 3 h and concentrated by centrifugal evaporation. The residues were dissolved in DMF (0.5 mL) and purified by HPLC on a C18 silica gel column, using acetonitrile/water gradients containing 0.05% trifluoroacetic acid as eluent. Compounds were isolated as trifluoroacetate salts and characterized by LCMS. All compounds exhibited appropriate molecular ions and fragmentation patterns. Those of 90% or greater purity were submitted for biological assessment. Selected compounds were analyzed by NMR spectroscopy, which confirmed their structural assignments.

TABLE 1

| Compound # | Compound Name | Calc. FB Mass | LCMS Mass (MH$^+$) |
|---|---|---|---|
| 1 | 2-((3-pyridinyl)methyl)-1-azabicyclo[2.2.2]oct-3-yl N-(4-bromophenyl)carbamate | 416.321 | 418.17 ($^{81}$Br) |
| 2 | 2-((3-pyridinyl)methyl)-1-azabicyclo[2.2.2]oct-3-yl N-phenylcarbamate | 337.425 | 338.34 |
| 3 | 2-((3-pyridinyl)methyl)-1-azabicyclo[2.2.2]oct-3-yl N-(4-fluorophenyl)carbamate | 355.416 | 356.30 |
| 4 | 2-((3-pyridinyl)methyl)-1-azabicyclo[2.2.2]oct-3-yl N-(4-methoxyphenyl)carbamate | 367.452 | 368.4 |
| 5 | 2-((3-pyridinyl)methyl)-1-azabicyclo[2.2.2]oct-3-yl N-(4-methylthiophenyl)carbamate | 383.516 | 384.29 |
| 6 | Levorotatory 2-((3-pyridinyl)methyl)-1-azabicyclo[2.2.2]oct-3-yl N-phenylcarbamate | 337.425 | 338.36 |
| 7 | Dextrorotatory 2-((3-pyridinyl)methyl)-1-azabicyclo[2.2.2]oct-3-yl N-phenylcarbamate | 337.425 | 338.37 |

Scale-up of 2-((3-pyridinyl)methyl)-1-azabicyclo[2.2.2]oct-3-yl(N-(4-bromophenyl)carbamate hydrochloride Compound 1

2-((3-Pyridinyl)methyl)-1-azabicyclo[2.2.2]octan-3-ol (0.218 g, 1.00 mmol) and p-bromophenylisocyanate (0.198 g, 1.00 mmol) were suspended in anhydrous toluene (2 mL) and heated at 180° C. for 5 min (microwave reactor). The volatiles were removed by rotary evaporation, and the residue was purified by flash (silica gel) column chromatography, using first chloroform/hexane/methanol/ammonia (68:25:7:1) and then chloroform/methanol/ammonia (90:10:1) as eluent. Concentration of selected fractions gave 0.260 g (62.5% yield) of colorless oil, which formed a waxy white solid upon standing at ambient temperature. NMR analysis confirmed that the material was predominantly the cis diastereomer. This material was dissolved in 4 M HCl in dioxane and concentrated to dryness, leaving a hygroscopic white solid.

The following example describes the synthesis of various N-(2-((3-pyridinyl)methyl)-1-azabicyclo[2.2.2]oct-3-yl) arylcarboxamides, which are built upon Scaffold 2. Table 2 shows a list of various compounds within this example that were synthesized.

Example 2

N-(2-((3-Pyridinyl)methyl)-1-azabicyclo[2.2.2]oct-3-yl)arylcarboxamides

Diphenylchlorophosphate (0.3 mmol) was added dropwise to solutions of various arylcarboxylic acids (0.3 mmol) and triethylamine (0.3 mmol) in dry dichloromethane (1 mL). After stirring at ambient temperature for 1 h, a solution of 3-amino-2-((3-pyridinyl)methyl)-1-azabicyclo[2.2.2]octane (0.3 mmol) and triethylamine (0.6 mmol) in dry dichloromethane (0.5 mL) was added to each of the mixed anhydride solutions. The reaction mixtures were stirred overnight at ambient temperature, then diluted with chloroform (2 mL) and washed with 5 M NaOH (2 mL). The organic layers were concentrated under reduced pressure, and the residues were dissolved in methanol (0.5 ml) and purified by HPLC on a C18 silica gel column, using acetonitrile/water gradients containing 0.05% trifluoroacetic acid as eluent. Compounds were isolated as trifluoroacetate salts and characterized by LCMS. All compounds exhibited appropriate molecular ions and fragmentation patterns. Those of 90% or greater purity were submitted for biological assessment. Selected compounds were analyzed by NMR spectroscopy, which confirmed their structural assignments.

TABLE 2

| Compound # | Compound Name | Calc. FB Mass | LCMS Mass (MH+) |
|---|---|---|---|
| 8 | N-(2-((3-pyridinyl)methyl)-1-azabicyclo[2.2.2]oct-3-yl)-4-fluorobenzamide | 339.416 | 340.31 |
| 9 | N-(2-((3-pyridinyl)methyl)-1-azabicyclo[2.2.2]oct-3-yl)benzofuran-2-carboxamide | 361.448 | 362.33 |
| 10 | N-(2-((3-pyridinyl)methyl)-1-azabicyclo[2.2.2]oct-3-yl)-4-bromobenzamide | 400.322 | 402.25 ($^{81}$Br) |
| 11 | N-(2-((3-pyridinyl)methyl)-1-azabicyclo[2.2.2]oct-3-yl)-4-phenylthiobenzamide | 429.589 | 430.30 |
| 12 | N-(2-((3-pyridinyl)methyl)-1-azabicyclo[2.2.2]oct-3-yl)-5-methylthiothiophene-2-carboxamide | 373.543 | 374.32 |
| 13 | N-(2-((3-pyridinyl)methyl)-1-azabicyclo[2.2.2]oct-3-yl)benzamide | 321.426 | 322.35 |
| 14 | N-(2-((3-pyridinyl)methyl)-1-azabicyclo[2.2.2]oct-3-yl)-3-methoxybenzamide | 351.452 | 352.37 |
| 15 | N-(2-((3-pyridinyl)methyl)-1-azabicyclo[2.2.2]oct-3-yl)-3-bromobenzamide | 400.322 | 402.24 ($^{81}$Br) |

Scale-up of N-(2-((3-pyridinyl)methyl)-1-azabicyclo[2.2.2]octan-3-yl)benzofuran-2-carboxamide Compound 9

Diphenylchlorophosphate (0.35 mL, 0.46 g, 1.69 mmol) was added drop-wise to a solution of the arylcarboxylic acid (0.280 g, 1.73 mmol) and triethylamine (0.24 mL, 0.17 g, 1.7 mmol) in dry dichloromethane (5 mL). After stirring at ambient temperature for 30 min, a solution of 3-amino-2-((3-pyridinyl)methyl)-1-azabicyclo[2.2.2]octane (0.337 g, 1.55 mmol) and triethylamine (0.24 mL, 0.17 g, 1.7 mmol) in dry dichloromethane (5 mL) was added. The reaction mixture was stirred overnight at ambient temperature, and then treated with 10% NaOH (1 mL). The biphasic mixture was separated by phase filtration, and the organic layer was concentrated on a Genevac centrifugal evaporator. The residue was dissolved in methanol (6 mL) and purified by HPLC on a C18 silica gel column, using an acetonitrile/water gradient containing 0.05% trifluoroacetic acid as eluent. Concentration of selected fractions gave 0.310 g (42% yield) of a white powder (95% pure by GCMS).

The following example describes the synthesis of various N-Aryl-N'-(2-((3-pyridinyl)methyl)-1-azabicyclo[2.2.2]oct-3-yl)ureas, which are built upon Scaffolds 2 and 3. Table 3 shows a list of various compounds within this example that were synthesized.

Example 3

N-Aryl-N'-(2-((3-Pyridinyl)methyl)-1-azabicyclo[2.2.2]oct-3-yl)ureas

Various arylisocyanates (0.3 mmol) were stirred with 3-amino-2-((3-pyridinyl)methyl)-1-azabicyclo[2.2.2]octane (0.3 mmol) in chloroform solution (1 mL) for 48 h at ambient temperature. The reaction mixtures were concentrated under reduced pressure, and the residues were dissolved in methanol (0.5 mL) and purified by HPLC on a C18 silica gel column, using acetonitrile/water gradients containing 0.05% trifluoroacetic acid as eluent. Compounds were isolated as trifluoroacetate salts and characterized by LCMS. All compounds exhibited appropriate molecular ions and fragmentation patterns. Those of 90% or greater purity were submitted for biological assessment. Selected compounds were analyzed by NMR spectroscopy, which confirmed their structural assignments.

Compounds possessing a methyl group on the nitrogen adjacent to the quinuclidine ring were prepared, by the same procedure as described above for unsubstituted ureas, using Scaffold 3.

TABLE 3

| Compound # | Compound Name | Calc. FB Mass | LCMS Mass (MH+) |
|---|---|---|---|
| 16 | N-phenyl-N'-(2-((3-pyridinyl) methyl)-1-azabicyclo[2.2.2]oct-3-yl)urea | 336.440 | 337.39 |
| 17 | N-(4-phenoxyphenyl)-N'-(2-((3-pyridinyl)methyl)-1-azabicyclo[2.2.2]oct-3-yl)urea | 428.539 | 429.36 |
| 18 | N-(4-methylthiophenyl)-N'-(2-((3-pyridinyl)methyl)-1-azabicyclo[2.2.2]oct-3-yl)urea | 382.532 | 383.34 |
| 19 | N-(3-fluorophenyl)-N'-(2-((3-pyridinyl)methyl)-1-azabicyclo[2.2.2]oct-3-yl)urea | 354.431 | 355.35 |
| 20 | N-(4-bromophenyl)-N'-(2-((3-pyridinyl)methyl)-1-azabicyclo[2.2.2]oct-3-yl)urea | 415.337 | 417.22 ($^{81}$Br) |
| 21 | N-(2-methoxyphenyl)-N'-(2-((3-pyridinyl)methyl)-1-azabicyclo[2.2.2]oct-3-yl)urea | 366.467 | 367.34 |
| 22 | N-(2,4-dimethoxyphenyl)-N'-(2-((3-pyridinyl)methyl)-1-azabicyclo[2.2.2]oct-3-yl)urea | 396.493 | 397.37 |
| 23 | N-(3,4-dichlorophenyl)-N'-(2-((3-pyridinyl)methyl)-1-azabicyclo[2.2.2]oct-3-yl)urea | 405.331 | 405.23 ($^{35}$Cl) |

TABLE 3-continued

| Compound # | Compound Name | Calc. FB Mass | LCMS Mass (MH+) |
|---|---|---|---|
| 24 | N-(4-methoxyphenyl)-N'-(2-((3-pyridinyl)methyl)-1-azabicyclo[2.2.2]oct-3-yl)urea | 366.467 | 367.34 |
| 25 | N-(4-dimethylaminophenyl)-N'-(2-((3-pyridinyl)methyl)-1-azabicyclo[2.2.2]oct-3-yl)urea | 379.509 | 380.40 |
| 26 | N-phenyl-N'-methyl-N'-(2-((3-pyridinyl)methyl)-1-azabicyclo[2.2.2]oct-3-yl)urea | 350.468 | 351.42 |
| 27 | N-(4-bromophenyl)-N'-methyl-N'-(2-((3-pyridinyl)methyl)-1-azabicyclo[2.2.2]oct-3-yl)urea | 429.364 | 431.26 ($^{81}$Br) |

The following example describes the synthesis of various N-(2-((3-pyridinyl)methyl)-1-azabicyclo[2.2.2]oct-3-yl)cinnamamides, which are built upon Scaffold 2. Table 4 shows a list of various compounds within this example that were synthesized.

Example 4

N-(2-((3-pyridinyl)methyl)-1-azabicyclo[2.2.2]oct-3-yl)cinnamamides

To a stirring solution of triethylamine (25 mL) in dry dichloromethane (0.5 mL) was added 3-amino-2-((3-pyridinyl)methyl)-1-azabicyclo[2.2.2]octane (0.040 g, 0.18 mmol). The mixture was cooled to 0° C. and stirred for 30 min. Then various cinnamoyl chlorides (0.18 mmol) were added and the mixtures allowed to stir at 0° C. for 30 min, then warm to room temperature and stir overnight. The mixtures were partitioned between saturated NaHCO$_3$ solution (25 mL) and chloroform (25 mL). The organic layers were washed with brine (3×5 mL), dried (Na$_2$SO$_4$) and concentrated by rotary evaporation. The residues were dissolved in methanol (0.5 mL) and purified by HPLC on a C18 silica gel column, using acetonitrile/water gradients containing 0.05% trifluoroacetic acid as eluent. Compounds were isolated as trifluoroacetate salts and characterized by LCMS. All compounds exhibited appropriate molecular ions and fragmentation patterns. Those of 90% or greater purity were submitted for biological assessment. Selected compounds were analyzed by NMR spectroscopy, which confirmed their structural assignments.

TABLE 4

| Compound # | Compound Name | Calc. FB Mass | LCMS Mass (MH+) |
|---|---|---|---|
| 28 | N-(2-((3-pyridinyl)methyl)-1-azabicyclo[2.2.2]oct-3-yl)3-phenylprop-2-enamide | 347.464 | 348.16 |
| 29 | N-(2-((3-pyridinyl)methyl)-1-azabicyclo[2.2.2]oct-3-yl)-3-(4-chlorophenyl)prop-2-enamide | 381.909 | 382.26 |
| 30 | N-(2-((3-pyridinyl)methyl)-1-azabicyclo[2.2.2]oct-3-yl)-3-(4-bromophenyl)prop-2-enamide | 426.360 | 428.20 ($^{81}$Br) |
| 31 | N-(2-((3-pyridinyl)methyl)-1-azabicyclo[2.2.2]oct-3-yl)-3-(3-hydroxyphenyl)prop-2-enamide | 363.463 | 364.35 |
| 32 | N-(2-((3-pyridinyl)methyl)-1-azabicyclo[2.2.2]oct-3-yl)-3-(3-methoxyphenyl) prop-2-enamide | 377.491 | 378.32 |
| 33 | N-(2-((3-pyridinyl)methyl)-1-azabicyclo[2.2.2]oct-3-yl)-3-(2-fluorophenyl)prop-2-enamide | 365.454 | 366.33 |
| 34 | N-(2-((3-pyridinyl)methyl)-1-azabicyclo[2.2.2]oct-3-yl)-3-(2-hydroxyphenyl)prop-2-enamide | 363.463 | 364.35 |

V. Biological Assays

Example 5

Radioligand Binding at CNS nAChRs

α4β2 nAChR Subtype

Rats (female, Sprague-Dawley), weighing 150-250 g, were maintained on a 12 h light/dark cycle and were allowed free access to water and food supplied by PMI Nutrition International, Inc. Animals were anesthetized with 70% $CO_2$, then decapitated. Brains were removed and placed on an ice-cold platform. The cerebral cortex was removed and placed in 20 volumes (weight:volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 µM, was added and the suspension was homogenized by Polytron. The homogenate was centrifuged at 18,000×g for 20 min at 4° C. and the resulting pellet was re-suspended in 20 volumes of ice-cold water. After 60 min incubation on ice, a new pellet was collected by centrifugation at 18,000×g for 20 min at 4° C. The final pellet was re-suspended in 10 volumes of buffer and stored at −20° C. On the day of the assay, tissue was thawed, centrifuged at 18,000×g for 20 min, and then re-suspended in ice-cold PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) to a final concentration of approximately 4 mg protein/mL. Protein was determined by the method of Lowry et al., *J. Biol. Chem.* 193: 265 (1951), using bovine serum albumin as the standard.

The binding of [$^3$H]nicotine was measured using a modification of the methods of Romano et al., *Science* 210: 647 (1980) and Marks et al., *Mol. Pharmacol.* 30: 427 (1986). The [$^3$H]nicotine (Specific Activity=81.5 Ci/mmol) was obtained from NEN Research Products. The binding of [$^3$H]nicotine was measured using a 3 h incubation at 4° C. Incubations were conducted in 48-well micro-titre plates and contained about 400 µg of protein per well in a final incubation volume of 300 µL. The incubation buffer was PBS and the final concentration of [$^3$H]nicotine was 5 nM. The binding reaction was terminated by filtration of the protein containing bound ligand onto glass fiber filters (GF/B, Brandel) using a Brandel Tissue Harvester at 4° C. Filters were soaked in de-ionized water containing 0.33% polyethyleneimine to reduce non-specific binding. Each filter was washed with ice-cold buffer (3×1 mL). Non-specific binding was determined by inclusion of 10 µM non-radioactive L-nicotine (Acros Organics) in selected wells.

The inhibition of [$^3$H]nicotine binding by test compounds was determined by including seven different concentrations of the test compound in selected wells. Each concentration was replicated in triplicate. $IC_{50}$ values were estimated as the concentration of compound that inhibited 50 percent of specific [$^3$H]nicotine binding. Inhibition constants (Ki values), reported in nM, were calculated from the $IC_{50}$ values using the method of Cheng et al., Biochem. Pharmacol. 22: 3099 (1973).

For initial screening, a single concentration of test compounds was tested in the above assay format with the following modifications. The binding of [$^3$H]epibatidine was measured. The [$^3$H]epibatidine (Specific Activity=48 Ci/mmol) was obtained from NEN Research Products. The binding of [$^3$H]epibatidine was measured using a 2 h incubation at 21° C. (room temperature). Incubations were conducted in 96-well Millipore Multiscreen (MAFB) plates containing about 200 µg of protein per well in a final incubation volume of 150 µL. The incubation buffer was PBS and the final concentration of [$^3$H]epibatidine was 0.3 nM. The binding reaction was terminated by filtration of the protein containing bound ligand onto the glass fiber filter base of the Multiscreen plates. Filters were soaked in de-ionized water containing 0.33% polyethyleneimine to reduce non-specific binding. Each filter was washed with ice-cold buffer (3×0.25 mL). Non-specific binding was determined by inclusion of 10 µM non-radioactive L-nicotine (Acros Organics) in selected wells. The single concentration of test compound was 5 µM and testing was performed in triplicate. 'Active' compounds were defined as compounds that inhibited the binding of [$^3$H]epibatidine to the receptor by at least 50% compared with the binding of [$^3$H]epibatidine in the absence of competitor. For those compounds found to be active in the single point screen, the inhibition constants (Ki values) were determined as described in the previous paragraphs of this section.

α7 nAChR Subtype

Rats (female, Sprague-Dawley), weighing 150-250 g, were maintained on a 12 h light/dark cycle and were allowed free access to water and food supplied by PMI Nutrition International, Inc. Animals were anesthetized with 70% $CO_2$, then decapitated. Brains were removed and placed on an ice-cold platform. The hippocampus was removed and placed in 10 volumes (weight:volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 µM, was added and the tissue suspension was homogenized by Polytron. The homogenate was centrifuged at 18,000×g for 20 min at 4° C. and the resulting pellet was re-suspended in 10 volumes of ice-cold water. After 60 min incubation on ice, a new pellet was collected by centrifugation at 18,000×g for 20 min at 4° C. The final pellet was re-suspended in 10 volumes of buffer and stored at −20° C. On the day of the assay, tissue was thawed, centrifuged at 18,000×g for 20 min, and then re-suspended in ice-cold PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) to a final concentration of approximately 2 mg protein/mL. Protein was determined by the method of Lowry et al., *J. Biol. Chem.* 193: 265 (1951), using bovine serum albumin as the standard.

The binding of [$^3$H]MLA was measured using a modification of the methods of Davies et al., Neuropharmacol. 38: 679 (1999). [$^3$H]MLA (Specific Activity=25-35 Ci/mmol) was obtained from Tocris. The binding of [$^3$H]MLA was determined using a 2 h incubation at 21° C. Incubations were conducted in 48-well micro-titre plates and contained about 200 µg of protein per well in a final incubation volume of 300 µL. The incubation buffer was PBS and the final concentration of [$^3$H]MLA was 5 nM. The binding reaction was terminated by filtration of the protein containing bound ligand onto glass fiber filters (GF/B, Brandel) using a Brandel Tissue Harvester at room temperature. Filters were soaked in de-ionized water containing 0.33% polyethyleneimine to reduce non-specific binding. Each filter was washed with PBS (3×1 mL) at room temperature. Non-specific binding was determined by inclusion of 50 µM non-radioactive MLA in selected wells.

The inhibition of [$^3$H]MLA binding by test compounds was determined by including seven different concentrations of the test compound in selected wells. Each concentration was replicated in triplicate. $IC_{50}$ values were estimated as the concentration of compound that inhibited 50 percent of specific [$^3$H]MLA binding. Inhibition constants (Ki values), reported in nM, were calculated from the $IC_{50}$ values using the method of Cheng et al., *Biochem. Pharmacol.* 22: 3099-3108 (1973).

For initial screening, a single concentration of test compounds was tested in the above assay format with the following modifications. Incubations were conducted in 96-well plates in a final incubation volume of 150 μL. Once the binding reaction was terminated by filtration onto glass fiber filters, the filters were washed four times with approximately 250 μL of PBS at room temperature. Non-specific binding was determined by inclusion of 10 μM non-radioactive MLA in selected wells. The single concentration of test compound was 5 μM and testing was performed in triplicate. 'Active' compounds were defined as compounds that inhibited the binding of [$^3$H]MLA to the receptor by at least 50% compared with the binding of [$^3$H]MLA in the absence of competitor. For those compounds found to be active in the single point screen, the inhibition constants (Ki values) were determined as described in the previous paragraphs of this section.

Determination of Dopamine Release

Dopamine release was measured using striatal synaptosomes obtained from rat brain, according to the procedures set forth by Rapier et al., *J. Neurochem.* 54: 937 (1990). Rats (female, Sprague-Dawley), weighing 150-250 g, were maintained on a 12 h light/dark cycle and were allowed free access to water and food supplied by PMI Nutrition International, Inc. Animals were anesthetized with 70% $CO_2$, then decapitated. The brains were quickly removed and the striata dissected. Striatal tissue from each of 2 rats was pooled and homogenized in ice-cold 0.32 M sucrose (5 mL) containing 5 mM HEPES, pH 7.4, using a glass/glass homogenizer. The tissue was then centrifuged at 1,000×g for 10 min. The pellet was discarded and the supernatant was centrifuged at 12,000×g for 20 min. The resulting pellet was re-suspended in perfusion buffer containing monoamine oxidase inhibitors (128 mM NaCl, 1.2 mM $KH_2PO_4$, 2.4 mM KCl, 3.2 mM $CaCl_2$, 1.2 mM $MgSO_4$, 25 mM HEPES, 1 mM ascorbic acid, 0.02 mM pargyline HCl and 10 mM glucose, pH 7.4) and centrifuged for 15 min at 25,000×g. The final pellet was resuspended in perfusion buffer (1.4 mL) for immediate use.

The synaptosomal suspension was incubated for 10 min at 37° C. to restore metabolic activity. [$^3$H]Dopamine ([$^3$H]DA, specific activity=28.0 Ci/mmol, NEN Research Products) was added at a final concentration of 0.1 μM and the suspension was incubated at 37° C. for another 10 min. Aliquots of tissue (50 μL) and perfusion buffer (100 μL) were loaded into the suprafusion chambers of a Brandel Suprafusion System (series 2500, Gaithersburg, Md.). Perfusion buffer (room temperature) was pumped into the chambers at a rate of 3 mL/min for a wash period of 8 min. Test compound (10 μM) or nicotine (10 μM) was then applied in the perfusion stream for 40 sec. Fractions (12 sec each) were continuously collected from each chamber throughout the experiment to capture basal release and agonist-induced peak release and to re-establish the baseline after the agonist application. The perfusate was collected directly into scintillation vials, to which scintillation fluid was added. [$^3$H]DA released was quantified by scintillation counting. For each chamber, the integrated area of the peak was normalized to its baseline.

Release was expressed as a percentage of release obtained with an equal concentration of L-nicotine. Within each assay, each test compound was replicated using 2-3 chambers; replicates were averaged. When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also defined.

Example 6

Selectivity vs. Peripheral nAChRs

Interaction at the Human Muscle nAChR Subtype

Activation of muscle-type nAChRs was established on the human clonal line TE671/RD, which is derived from an embryonal rhabdomyosarcoma (Stratton et al., Carcinogen 10: 899 (1989)). These cells express receptors that have pharmacological (Lukas, *J. Pharmacol. Exp. Ther.* 251: 175 (1989)), electrophysiological (Oswald et al., *Neurosci. Lett.* 96: 207 (1989)), and molecular biological profiles (Luther et al., *J. Neurosci.* 9: 1082 (1989)) similar to the muscle-type nAChR.

TE671/RD cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 6 well polystyrene plates (Costar). Experiments were conducted when the cells reached 100% confluency.

Nicotinic acetylcholine receptor (nAChR) function was assayed using $^{86}Rb^+$ efflux according to the method described by Lukas et al., *Anal. Biochem.* 175: 212 (1988). On the day of the experiment, growth media was gently removed from the well and growth media containing $^{86}$Rubidium chloride ($10^6$ μCi/mL) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH. 7.4), taking care not to disturb the cells. Next, cells were exposed to either 100 μM of test compound, 100 μM of L-nicotine (Acros Organics) or buffer alone for 4 min. Following the exposure period, the supernatant containing the released $^{86}Rb^+$ was removed and transferred to scintillation vials. Scintillation fluid was added and released radioactivity was measured by liquid scintillation counting.

Within each assay, each point had 2 replicates, which were averaged. The amount of $^{86}Rb^+$ release was compared to both a positive control (100 μM L-nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also determined.

Interaction at the Rat Ganglionic nAChR Subtype

Activation of rat ganglion nAChRs was established on the pheochromocytoma clonal line PC12, which is a continuous clonal cell line of neural crest origin, derived from a tumor of the rat adrenal medulla. These cells express ganglion-like nAChR s (see Whiting et al., *Nature* 327: 515 (1987); Lukas, *J. Pharmacol. Exp. Ther.* 251: 175 (1989); Whiting et al., *Mol. Brain Res.* 10: 61 (1990)).

Rat PC12 cells were maintained in proliferative growth phase according to routine protocols (Bencherif et al., *Mol.*

Cell. Neurosci. 2: 52 (1991) and Bencherif et al., J. Pharmacol. Exp. Ther. 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 6 well Nunc plates (Nunclon) and coated with 0.03% poly-L-lysine (Sigma, dissolved in 100 mM boric acid). Experiments were conducted when the cells reached 80% confluency.

Nicotinic acetylcholine receptor (nAChR) function was assayed using $^{86}Rb^+$ efflux according to a method described by Lukas et al., Anal. Biochem. 175: 212 (1988). On the day of the experiment, growth media was gently removed from the well and growth media containing $^{86}$Rubidium chloride ($10^6$ μCi/mL) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH. 7.4), taking care not to disturb the cells. Next, cells were exposed to either 100 μM of test compound, 100 μM of nicotine or buffer alone for 4 min. Following the exposure period, the supernatant containing the released $^{86}Rb^+$ was removed and transferred to scintillation vials. Scintillation fluid was added and released radioactivity was measured by liquid scintillation counting Within each assay, each point had 2 replicates, which were averaged. The amount of $^{86}Rb^+$ release was compared to both a positive control (100 μM nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also determined.

Interaction at the Human Ganglionic nAChR Subtype

The cell line SH-SY5Y is a continuous line derived by sequential subcloning of the parental cell line, SK-N-SH, which was originally obtained from a human peripheral neuroblastoma. SH-SY5Y cells express a ganglion-like nAChR (Lukas et al., Mol. Cell. Neurosci. 4: 1 (1993)).

Human SH-SY5Y cells were maintained in proliferative growth phase according to routine protocols (Bencherif et al., Mol. Cell. Neurosci. 2: 52 (1991) and Bencherif et al., J. Pharmacol. Exp. Ther. 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 6 well polystyrene plates (Costar). Experiments were conducted when the cells reached 100% confluency.

Nicotinic acetylcholine receptor (nAChR) function was assayed using $^{86}Rb^+$ efflux according to a method described by Lukas et al., Anal. Biochem. 175: 212 (1988). On the day of the experiment, growth media was gently removed from the well and growth media containing $^{86}$Rubidium chloride ($10^6$ μCi/mL) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH. 7.4), taking care not to disturb the cells. Next, cells were exposed to either 100 μM of test compound, 100 μM of nicotine, or buffer alone for 4 min. Following the exposure period, the supernatant containing the released $^{86}Rb^+$ was removed and transferred to scintillation vials. Scintillation fluid was added and released radioactivity was measured by liquid scintillation counting Within each assay, each point had 2 replicates, which were averaged. The amount of $^{86}Rb^+$ release was compared to both a positive control (100 μM nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also defined.

Example 7

Determination of Binding at Non-nicotinic Receptors

Muscarinic M3 Subtype

The human clonal line TE671/RD, derived from an embryonal rhabdomyosarcoma (Stratton et al., Carcinogen 10: 899 (1989)), was used to define binding to the muscarinic M3 receptor subtype. As evidenced through pharmacological (Bencherif et al., J. Pharmacol. Exp. Ther. 257: 946 (1991) and Lukas, J. Pharmacol. Exp. Ther. 251: 175 (1989)), electrophysiological (Oswald et al., Neurosci. Lett. 96: 207 (1989)), and molecular biological studies (Luther et al., J. Neurosci. 9: 1082 (1989)) these cells express muscle-like nicotinic receptors.

TE671/RD cells were maintained in proliferative growth phase according to routine protocols (Bencherif et al., Mol. Cell. Neurosci. 2: 52 (1991) and Bencherif et al., J. Pharmacol. Exp. Ther. 257: 946 (1991)). They were grown to confluency on 20-150 mm tissue culture treated plates. The media was then removed and cells scraped using 80 mL of PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) and then centrifuged at 1000 rpm for 10 min. The supernatant was then suctioned off and the pellet(s) stored at −20° C. until use.

On the day of the assay, the pellets were thawed, re-suspended with PBS and centrifuged at 18,000×g for 20 min, then re-suspended in PBS to a final concentration of approximately 4 mg protein/mL and homogenized by Polytron. Protein was determined by the method of Lowry et al., J. Biol. Chem. 193: 265 (1951), using bovine serum albumin as the standard.

The binding of [$^3$H]QNB was measured using a modification of the methods of Bencherif et al., J. Pharmacol. Exp. Ther. 257: 946 (1991). [$^3$H]QNB (Specific Activity=30-60 Ci/mmol) was obtained from NEN Research Products. The binding of [$^3$H]QNB was measured using a 3 h incubation at 4° C. Incubations were conducted in 48-well micro-titre plates and contained about 400 μg of protein per well in a final incubation volume of 300 μL. The incubation buffer was PBS and the final concentration of [$^3$H]QNB was 1 nM. The binding reaction was terminated by filtration of the protein containing bound ligand onto glass fiber filters (GF/B, Brandel) using a Brandel Tissue Harvester at 4° C. Filters were pre-soaked in de-ionized water containing 0.33% polyethyleneimine to reduce non-specific binding. Each filter was washed with ice-cold buffer (3×1 mL). Non-specific binding was determined by inclusion of 10 µM non-radioactive atropine in selected wells.

The inhibition of [³H]QNB binding by test compounds was determined by including seven different concentrations of the test compound in selected wells. Each concentration was replicated in triplicate. $IC_{50}$ values were estimated as the concentration of compound that inhibited 50 percent of specific [³H]QNB binding. Inhibition constants (Ki values), reported in nM, were calculated from the $IC_{50}$ values using the method of Cheng et al., *Biochem. Pharmacol.* 22: 3099 (1973).

Example 8

Determination of Activity at the α7 nAChR subtype

Selective α7 agonists can be found using a functional assay on FLIPR (see, for example, PCT WO 00/73431 A2, the contents of which are hereby incorporated by reference), which is a commercially available high throughput assay (Molecular Devices Corporation, Sunnyvale, Calif.). FLIPR is designed to read the fluorescent signal from each well of a 96 or 384 well plate as fast as twice a second for up to 30 minutes. This assay can be used to accurately measure the functional pharmacology of α7 nAChR and $5HT_3R$ subtypes. Cell lines that express functional forms of the α7 nAChR subtype using the α7/5-$HT_3$ channel as the drug target and/or cell lines that express functional 5-$HT_3$ are used to conduct the assay. In both cases, the ligand-gated ion channels are expressed in SH-EP1 cells. Both ion channels can produce a robust signal in the FLIPR assay. Using the FLIPR assay, the compounds described herein can be evaluated for their ability to function as agonists, partial agonists or antagonists at the α7 nAChR subtype.

Example 9

Summary of Biological Activity

Compounds 1-34 competitively inhibited the binding of radiolabeled MLA to rat brain hippocampus α7 nAChR subtypes with an equilibrium constant (Ki) values of 0.5-60 nM, indicating that they have very high affinity for the α7 nAChR subtype. High-throughput screening indicated that none of the compounds bound to α4β2 nAChR subtypes with any significant affinity (Ki values>10 µM).

Compounds 1-34 exhibited little or no agonist activity in functional models bearing muscle-type receptors (α3β1γι subtype in human TE671/RD clonal cells), or ganglion-type receptors (α3β4 subtype in the Shooter subclone of rat pheochromocytoma PC12 cells and in human SHSY-5Y clonal cells), generating only 1-12% (human muscle), 1-19% (rat ganglion) and 1-15% (human ganglion) of nicotine's response at these subtypes. These data indicate selectivity for CNS over PNS nAChRs. Because similar compounds had been described by others as exhibiting muscarinic activity (see, for instance, U.S. Pat. No. 5,712,270 to Sabb and PCTs WO 02/00652 and WO 02/051841), representative compounds (#s 1, 2, 4, 9 and 11) were evaluated for their ability to inhibit [³H]QNB binding at muscarinic sites in the human clonal line TE671/RD. None of the compounds was able to inhibit [³H]QNB binding, indicating that these compounds do not bind to human M3 receptors. Thus, compounds of the present invention are distinguished in their in vitro pharmacology from reference compounds (see, for instance, U.S. Pat. No. 5,712,270 to Sabb and PCTs WO 02/00652 and WO 02/051841) by virtue of the inclusion, in their structure, of the 3-pyridinylmethyl substituent in the 2 position of the 1-azabicycle.

Following up on this intriguing finding, a comparison of α7 nAChR binding affinities was undertaken, to determine the effect of the 2-(3-pyridinyl)methyl substituent. The results are shown in Table 5. It is clear from the data that inclusion of the 2-(3-pyridinyl)-$C_{1-4}$alkyl, preferably 2-(3-pyridinyl)methyl, substituent in the structure substantially increases binding affinity. Thus, compounds of the present invention exhibit both greater affinity at and greater selectivity for α7 nAChR subtypes than those compounds which lack the 2-(3-pyridinyl)alkyl, preferably 2-(3-pyridinyl)methyl, substituent.

TABLE 5

| Structure | a7 Ki (nM) |
|---|---|
| 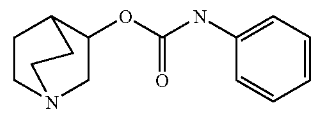 | 120 |
| 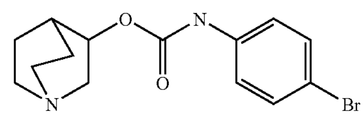 | 40 |
| 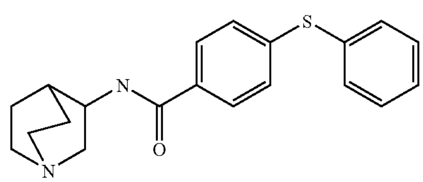 | 53 |
| 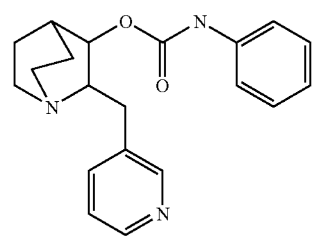 | 7 |
| 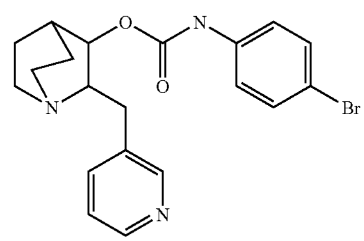 | 5 |
| 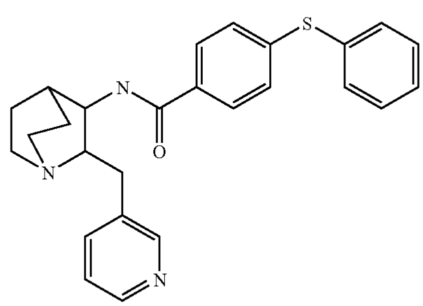 | 9 |

The data show that the compounds of the present invention are potent α7 nicotinic ligands that selectively bind at α7 nAChR subtypes. In contrast, the compounds of the present invention do not bind well at those subtypes of the nAChR that are characteristic of the peripheral nervous system or at M3 muscarinic receptors. Thus, the compounds of the present invention possess therapeutic potential in treating central nervous system disorders without producing side effects associated with interaction with the peripheral nervous system. The affinity of these ligands for α7 nAChR subtypes is tolerant of a wide variety of aryl (Ar in Formula 1) groups and substituents thereon. Furthermore, the synthesis is straightforward, efficient and amenable to massively parallel protocols.

Having disclosed the subject matter of the present invention, it should be apparent that many modifications, substitutions and variations of the present invention are possible in light thereof. It is to be understood that the present invention can be practiced other than as specifically described. Such modifications, substitutions and variations are intended to be within the scope of the present application.

That which is claimed is:

1. A method for the treatment of one or more of pre-senile dementia and senile dementia comprising administering a therapeutically effective amount of (R,R; R,S; S,R; and S,S)—N-(2-((3-pyridinyl)methyl)-1-azabicyclo[2.2.2]oct-3-yl)benzofuran-2-carboxamide or a pharmaceutically acceptable salt thereof.

* * * * *